United States Patent
Case et al.

(10) Patent No.: US 7,491,531 B2
(45) Date of Patent: *Feb. 17, 2009

(54) RANDOMIZED LIBRARIES OF ZINC FINGER PROTEINS

(75) Inventors: Casey C. Case, San Mateo, CA (US); Edward J. Rebar, El Cerrito, CA (US); Andrew Jamieson, San Francisco, CA (US)

(73) Assignee: Sangamo BioSciences, Inc., Richmond, CA (US)

( * ) Notice: Subject to any disclaimer, the term of this patent is extended or adjusted under 35 U.S.C. 154(b) by 1106 days.

This patent is subject to a terminal disclaimer.

(21) Appl. No.: 10/337,216

(22) Filed: Jan. 6, 2003

(65) Prior Publication Data

US 2003/0134318 A1 Jul. 17, 2003

Related U.S. Application Data

(63) Continuation of application No. 09/731,558, filed on Dec. 6, 2000, now Pat. No. 6,503,717, which is a continuation-in-part of application No. 09/456,100, filed on Dec. 6, 1999, now abandoned.

(51) Int. Cl.
  C12N 15/11 (2006.01)
  C12N 15/63 (2006.01)
  C12N 15/79 (2006.01)
(52) U.S. Cl. ............... 435/325; 435/419; 435/320.1
(58) Field of Classification Search ............ 435/325, 435/320.1
  See application file for complete search history.

(56) References Cited

U.S. PATENT DOCUMENTS

| | | | |
|---|---|---|---|
| 4,990,607 A | 2/1991 | Katagiri et al. |
| 5,096,814 A | 3/1992 | Aivasidis et al. |
| 5,096,815 A | 3/1992 | Ladner et al. |
| 5,173,414 A | 12/1992 | Lebkowski et al. |
| 5,198,346 A | 3/1993 | Ladner et al. |
| 5,223,409 A | 6/1993 | Ladner et al. |
| 5,243,041 A | 9/1993 | Fernandez-Pol |
| 5,302,519 A | 4/1994 | Blackwood et al. |
| 5,324,638 A | 6/1994 | Tao et al. |
| 5,324,818 A | 6/1994 | Nabel et al. |
| 5,324,819 A | 6/1994 | Oppermann et al. |
| 5,340,739 A | 8/1994 | Stevens et al. |
| 5,348,864 A | 9/1994 | Barbacid |
| 5,350,840 A | 9/1994 | Call et al. |
| 5,356,802 A | 10/1994 | Chandrasegaran |
| 5,376,530 A | 12/1994 | De The et al. |
| 5,403,484 A | 4/1995 | Ladner et al. |
| 5,436,150 A | 7/1995 | Chandrasegaran |
| 5,487,994 A | 1/1996 | Chandrasegaran |
| 5,498,530 A | 3/1996 | Schatz et al. |
| 5,578,483 A | 11/1996 | Evans et al. |
| 5,597,693 A | 1/1997 | Evans et al. |
| 5,639,592 A | 6/1997 | Evans et al. |
| 5,674,738 A | 10/1997 | Abramson et al. |
| 5,702,914 A | 12/1997 | Evans et al. |
| 5,789,538 A | 8/1998 | Rebar et al. |
| 5,792,640 A | 8/1998 | Chandrasegaran |
| 5,869,618 A | 2/1999 | Lippman et al. |
| 5,871,902 A | 2/1999 | Weininger et al. |
| 5,871,907 A | 2/1999 | Winter et al. |
| 5,916,794 A | 6/1999 | Chandrasegaran |
| 5,939,538 A | 8/1999 | Leavitt et al. |
| 5,972,615 A | 10/1999 | An et al. |
| 6,001,885 A | 12/1999 | Vega et al. |
| 6,007,988 A | 12/1999 | Choo et al. |
| 6,013,453 A | 1/2000 | Choo et al. |

FOREIGN PATENT DOCUMENTS

| | | |
|---|---|---|
| EP | 0 873 567 A2 | 4/1998 |
| WO | WO 94/05700 | 3/1994 |
| WO | WO 95/19431 | 7/1995 |
| WO | WO 96/06110 | 2/1996 |
| WO | WO 96/06166 | 2/1996 |
| WO | WO 96/11267 | 4/1996 |
| WO | WO 96/20951 | 7/1996 |
| WO | WO 96/32475 | 10/1996 |
| WO | WO 97/27212 | 7/1997 |
| WO | WO 97/27213 | 7/1997 |
| WO | WO 98/53057 | 11/1998 |
| WO | WO 98/53058 | 11/1998 |
| WO | WO 98/53059 | 11/1998 |
| WO | WO 98/53060 | 11/1998 |
| WO | WO 98/54311 | 12/1998 |
| WO | WO 99/35494 | 7/1999 |
| WO | WO 99/36553 | 7/1999 |
| WO | WO 99/41371 | 8/1999 |
| WO | WO 99/42474 | 8/1999 |
| WO | WO 99/45132 | 9/1999 |
| WO | WO 99/47656 | 9/1999 |
| WO | WO 99/48909 | 9/1999 |
| WO | WO 00/23464 | 4/2000 |
| WO | WO 00/27878 | 5/2000 |

OTHER PUBLICATIONS

Agarwal et al., "Stimulation of Transcript Elongation Requires Both the Zinc Finger and RNA Polymerase II Binding Domains of Human TFIIS," *Biochemistry* 30(64):7842-7851 (1991).

Antao et al., "A Thermodynamic Study of Unusually Stable RNA and DNA Hairpins," *Nuc. Acids. Res.* 19(21):5901-5905 (1991).

Barbas, C. F., "Recent Advances in Phage Display," *Curr. Opin. Biotech.* 4:526-530 (1993).

Barbas et al., "Assembly of Combinatorial Antibody Libraries on Phage Surfaces: The Gene III Site," *PNAS* 88:7978-7982 (1991).

Barbas et al., "Semisynthetic Combinatorial Antibody Libraries: A Chemical Solution to the Diversity Problem," *PNAS* 89:4457-4461 (1992).

(Continued)

*Primary Examiner*—John S Brusca
(74) *Attorney, Agent, or Firm*—Robins & Pasternak LLP

(57) ABSTRACT

The present invention relates to methods of using libraries of randomized zinc finger proteins to identify genes associated with selected phenotypes.

10 Claims, 5 Drawing Sheets

OTHER PUBLICATIONS

Beerli et al., "Toward Controlling Gene Expression at Will: Specific Regulation of the erbB-2/HER-2 Promoter by Using Polydactyl Zinc Finger Proteins Constructed From Modular Building Blocks," *Proc. Natl. Acad. Sci. U.S.A.* 95:14628-14633 (1998).

Bellefroid et al., "Clustered Organization of Homologous KRAB Zinc-Finger Genes With Enhanced Expression in Human T Lymphoid Cells," *EMBO J.* 12(4):1363-1374 (1993).

Berg, J.M., "DNA Binding Specificity of Steroid Receptors," *Cell* 57:1065-1068 (1989).

Berg, J.M., "Sp1 and the Subfamily of Zinc-Finger Proteins with Guanine-Rich Binding Sites," *PNAS* 89:11109-11110 (1992).

Berg et al., "The Galvanization of Biology: A Growing Appreciation for the Roles of Zinc," *Science* 271:1081-1085 (1996).

Berg, J.M., "Letting Your Fingers do the Walking," *Nature Biotechnology* 15:323 (1997).

Bergqvist et al., "Loss of DNA-binding and new Transcriptional Trans-Activation Function in Polyomavirus Large T-Antigen with Mutation of Zinc Finger Motif," *Nuc. Acids Res.* 18(9):2715-2720 (1990).

Blaese et al., "Vectors in Cancer Therapy: How Will They Deliver?," *Cancer Gene Therapy* 2(4):291-297 (1995).

Buchscher et al., "Human Immunodeficiency Virus Vectors for Inducible Expression of Foreign Genes," *Journal of Virology* 66(5):2731-2739 (1992).

Caponigro et al., "Transdominant Genetice Analysis of a Growth Control Pathyway," *Proc. Natl. Acad. Sci. U.S.A.* 95:7508-7513 (1998).

Celenza et al., "A Yeast Gene That Is Essential for Release from Glucose Repression Encodes a Protein Kinase," *Science* 233:1175-1180 (1986).

Cheng et al., "Identification of Potential Target Genes for Adrip through Characterization of Essential Nucleotides in UASI," *J. Mol. Cellular Biol.* 14(6):3842-3852 (1994).

Cheng et al., "A Single Amino Acid Substitution in Zinc Finger 2 of Adrip Changes its Binding Specificity at two Positions in UAS1," *J. Mol. Biol.* 251:1-8 (1995).

Choo et al., A Role in DNA-Binding for the Linker Sequences of the First Three Zinc Fingers of TFIIIA *Nuc. Acids Res.* 21(15):3341-3346 (1993).

Choo et al., "Promoter-Specific Activation of Gene Expression Directed By Bacteriophage-Selected Zinc Fingers," *J. Mol. Biol.* 273:525-532 (1997).

Choo et al., "Designing DNA-Binding Proteins on the Surface of Filamentous Phage," *Curr. Opin. Biotechnology* 6:431-436 (1995).

Choo, Y., "Recognition of DNA Methylation by Zinc Fingers," *Nature Struct Biol.* 5(4):264-365 (1998).

Choo et al., "All Wrapped Up," *Nature Structural Biology* 5(4):253-255 (1998).

Choo, Y., "End Effects in DNA Recognition by Zinc Finger Arrays," *Nuc. Acids. Res.* 26(2):554-557 (1998).

Choo et al., Physical Basis of Protein-DNA Recognition Code, *Curr. Opin. Struct. Biol.* 7(1):117-125 (1997).

Choo et al., "In Vivo Repression by a Site-Specific DNA-Binding Protein Designed Against an Oncogenic Sequence," *Nature* 372:642-645 (1994).

Choo et al., "Selection of DNA Binding Sites for Zinc Fingers Using Rationally Randomized DNA Reveals Coded Interactions," *Proc. Natl. Acad. Sci. U.S.A.* 91:11168-11172 (1994).

Choo et al., "Toward a Code for the Interactions of Zinc Fingers With DNA: Selection of Randomized Fingers Displayed on Phage," *Proc. Natl. Acad. Sci. U.S.A.* 91:11163-11167.

Clark et al., "Zinc Fingers in *Caenorhabditis elegans*: Finding Families and Probing Pathways," *Science* 282:2018-2022 (1998).

Corbi et al., "Synthesis of a New Zinc Finger Peptide: Comparison of Its "Cod" Deduced and CASTing Derived Binding Sites," *FEBS Letters* 417:71-74 (1997).

Crozatier et al., "Single Amino Acid Exchanges in Separate Domains of the Drosophila Serendipity δ Zinc Finger Protein Cause Embroyonic and Sex Biased Lethality," *Genetics* 131:905-916 (1992).

Debs et al., Regulation of Gene Expression in Vivo by Liposome-Mediated Delivery of a Purified Transcription Factor, *J. Biological Chemistry* 265(18):10189-10192 (1990).

Desjarlais et al., "Redesigning the DNA-Binding Specificity of a Zinc Finger Protein: A Data Base-Guided Approach," *Proteins: Structure, Function, and Genetics* 12(2):101-104 (1992).

Desjarlais et al., "Redesigning the DNA-Binding Specificity of a Zinc Finger Protein: A Data Base-Guided Approach," *Proteins: Structure, Function, and Genetics* 13(3):272 (1992).

Desjarlais, J. R. and Berg, J.M., "Length-Encoded Multiplex binding Suite Determination: Application to Zinc Finger Proteins," *Proc. Natl. Acad. Sci. U.S.A.* 91:11099-11103 (1994).

Desjarlais, J. R. and Berg, J.M., "Use of a Zinc-Finger Consensus Sequence Framework and Specificity Rules to Design Specific DNA Binding Proteins," *Proc. Natl. Acad. Sci. U.S.A.* 90:2256-2260 (1993).

Desjarlais, J. R. and Berg, J.M., "Toward Rules Relating Zinc Finger Protein-Sequences and DNA Binding Preferences," *Proc. Natl. Acad. Sci. U.S.A.* 89:7345-4349 (1992).

Dibello et al., "The Drosophila *Broad-Complex* Encodes a Family of Related Proteins Containing Zinc Fingers," *Genetics* 129:385-397 (1991).

Elrod-Erickson et al., "High-Resolution Structures of Variant Zif268-DNA Complexes: Implications for Understanding Zinc Finger-DNA Recognition," *Structure* 6:(4):451-464 (1998).

Elrod-Erickson et al., "Zif268 Protein-DNA Complex Refined at 1.6 A: a Model System for Understanding Zinc Finger-DNA Interactions," *Structure* 4(10):1171-1180 (1996).

Fairall et al., "The Crystal Structure of a Two Zinc-Finger Peptide Reveals an Extension to the Rules for Zinc-Finger /DNA Recognition," *Nature* 366:483-487 (1993).

Frankel et al., "Fingering Too Many Proteins," *Cell* 53:675 (1988).

Friesen et al., "Phage Display of RNA Binding Zinc Fingers from Transcription Factor IIA*," *J. Biological Chem.* 272(17):10994-10997 (1997).

Friesen et al., "Specific RNA Binding Proteins Constructed from Zinc Fingers," *Nature Structural Biology* 5(7):543-546 (1998).

Gillemans et al., "Altered DNA Binding Specificity Mutants of EKLF and Sp1 Show that EKLF is an Activator of the b-globin locus Control Region in vivo," *Genes and Development* 12:2863-2873 (1998).

Gogos et al., "Recognition of Diverse Sequences by Class I Zinc Fingers: Asymmetries and Indirect Effects on Specificity in the Interaction Between CF2II and A+T-Rich Sequences Elements," *PNAS* 93(5):2159-2164 (1996).

Goldfarb et al., "Isolation and Preliminary Characterization of a Human Transforming Gene From T24 Bladder Carcinoma Cells," *Nature* 296:404- (1982).

Gossen et al., "Tight Control of Gene Expression in Mammalian Cells by Tetracycline-Responsive Promoter," *PNAS* 89:5547-5551 (1992).

Greisman & Pabo, "A General Strategy for Selecting High-Affinity Zinc Finger Proteins for Diverse DNA Target Sites," *Science* 275:657-661 (1997).

Hamilton et al., "High Affinity Binding Sites for the Wilms' Tumor Suppressor Protein WTI," *Nuc. Acids. Res.* 23(2):277-284 (1995).

Hamilton et al., "Comparison of the DNA Binding Characteristics of the Related Zinc Finger Proteins WT1 and EGR1," *Biochemistry* 37:2051-2058 (1998).

Hanas et al., "Internal Deletion Mutants of *Xenopus* Transcription Factor IIIa," *Nuc. Acids. Res.* 17(23):9861-9870 (1989).

Hannon et al., "MaRX: An Approach to Genetics in Mammalian Cells," *Science* 283:1129-1130 (1999).

Hayes et al., "Locations of Contacts Between Individual Zinc Fingers *Xenopus laevis* Transcription Factor IIIA and the Internal Control Region of a 5S RNA Gene," *Biochemistry* 31:11600-11605 (1992).

Heinzel et al., "A Complex containing N-CoR, MSin3 and Histone Deacetylese Medates Transcriptional Repression," *Nature* 387:43-48 (1997).

Hermonat & Muzyczka, "Use of Adeno-Associated Virus as a Mammallan DNA Cloning Vector: Transduction of Neomycin Resistance into Mammalian Tissue Culture Cells," *Proc. Natl. Acad. Sci. U.S.A.* 81:6466-6470 (1984).

Hirst et al., "Discrimination of DNA Response Elements for Thyroid Hormone and Estrogen is Dependent on Dimerization of Receptor DNA Binding Domains," *PNAS* 89:5527-5531 (1992).

Hoffman et al., "Structures of DNA-Binding Mutant Zinc Finger Domains: Implications for DNA Binding," *Protein Science* 2:951-965 (1993).

Imhof et al., "Transcriptional Regulation of the AP-Zalpha Promoter by BTEB-1 and AP-ZREP, a Novel WT-1/EGR-Related Zinc Finger Repressor," *Molecular and Cellular Biology* 19(1):194-204 (1999).

Isalan et al., "Synergy Between Adjacent Zinc Fingers in Sequence-Specific DNA Recognition," *PNAS* 94(11):5617-5621 (1997).

Isalan et al., "Comprehensive DNA Recognition Through Concerted Interactions from Adjacent Zinc Fingers," *Biochemistry* 37:12026-12033 (1998).

Jacobs, G.H., "Determination of the Base Recognition Positions of Zinc Fingers From Sequence Analysis," *EMBO J.* 11(12):4507-4517 (1992).

Jamieson et al. "A Zinc Finger Directory for High-Affinity DNA Recognition," *PNAS* 93:12834-12839 (1996).

Jamieson et al., "In Vitro Selection of Zinc Fingers with Altered DNA-Binding Specificity," *Biochemistry* 33:5689-5695 (1994).

Johann et al., "GLVR1, a Receptor for Gibbon Ape Leukemia Virus, Is Homologous to a Phosphate Permease of *Neurospora crassa* and Is Expressed in High Levels in the Brain and Thymus," *Journal of Virology* 66(3):1635-1640 (1992).

Julian et al., "Replacement of His23 by Cys in a Zinc Finger of HIV-1NCp7 Led to a Change in 1H NMR-Derived 3D Structure and to a Loss of Biological Activity," *FEBS Letters* 331(1,2):43-48 (1993).

Kamiuchi et al., "New Multi Zinc Finger Protein: Biosynthetic Design and Characteristics of DNA Recognition," *Nucleic Acids Symposium Series* 37:153-154 (1997).

Kang et al., "Zinc Finger Proteins as Designer Transcription Factors," *J. Biol. Chem.* 275(12):8742-8748 (2000).

Kim et al., "Serine at Position 2 in the DNA Recognition Helix of a Cys2-His2 Zinc Finger Peptide is Not, in General, Responsible for Base Recognition," *J. Mol. Biol.* 252:1-5 (1995).

Kim et al., "Site-Specific Cleavage of DNA-RNA Hybrids by Zinc Finger/*Fok*/Cleavage Domain Fusions," *Gene* 203:43-49 (1997).

Kim et al., "A 2.2 A° Resolution Crystal Structure of a Designed Zinc Finger Protein Bound to DNA," *Nat. Struct. Biol.* 3(11):940-945 (1996).

Kim et al., "Design of TATA Box-Binding Protein/Zinc Finger Fusions for Targeted Regulation of Gene Expression," *PNAS* 94:3616-3620 (1997).

Kim et al., "Hybrid Restriction Enzymes: Zinc Finger Fusions *Fok* I Cleavage Domain," *PNAS* 93:1156-1160 (1996).

Kim, J.S. and Pabo, C.O., "Getting a Handhold on DNA: Design of Poly-Zinc finger Proteins with Femtomolar Dissociation Constants," *Proc. Natl. Acad. Sci. U.S.A.* 95:2812-2817 (1998).

Kim, J.S. and Pabo, C.O., "Transcriptional Repression by Zinc Finger Peptides," *The Journal of Biological Chemistry* 272:29795-28000 (1997).

Kinzler et al., "The GLI Gene is Member of the Kruppel Family of Zinc Finger Proteins," *Nature* 332:371-374 (1988).

Klug, A., "Gene Regulatory Proteins and Their Interaction with DNA," *Ann. NY Acad. Sci.* 758:143-160 (1995).

Klug et al., "Protein Motifs 5: Zinc Fingers," *FASEB J.* 9:597-604 (1995).

Klug, "Zinc Finger Peptides for the Regulation of Gene Expression," *J. Mol. Biol.* 293:215-218 (1999).

Kothekar, "Computer Simulation of Zinc Finger Motifs from Cellular Nucleic Acid Binding Proteins and their Interaction with Consensus DNA Sequences," *FEBS Letters* 274(1,2):217-222 (1990).

Kriwacki et al., "Sequence-Specific Recognition of DNA by Zinc-Finger Peptides Derived From the Transcription Factor Sp1," *Proc. Natl. Acad. Sci. U.S.A.* 89:9759-9763 (1992).

Kulda et al., "The Regulatory Gene *are*A Mediating Nitrogen Metabolite R in *Aspergillus nidulans* Mutations Affecting Specificity of Gene Activation Alter a Loop Residue of Putative Zinc Finger," *EMBO J.* 9(5):1355-1364 (1990).

Laird-Offringa et al., "RNA-Binding Proteins Tamed," *Nat. Structural Biol.* 5(8):665-668 (1998).

Liu et al., "Design of Polydactyl Zinc-Finger Proteins for Unique Addressing Within Complex Genomes," *Proc. Natl. Acad. Sci. U.S.A.* 94:5525-5530 (1997).

Liu et al., "Regulation of an Endogenous Locus Using a Panel of Designed Zinc Finger Proteins Targeted to Accessible Chromatin Regions: Activation of Vascular Endothelial Growth Factor A," *Journal of Biological Chemistry* 276(14):11323-11334 (2001).

Liu et al., "Transcription Factor EGR-1 Suppresses the Growth and Transformation of Human HT-1080 Fibrosarcoma Cells by Induction of Transforming Growth Factor Beta 1," *Proceedings of the National Academy of Sciences of USA,US, National Academy of Science, Washington* 93(21):11831-11836 (1996).

Mandel-Gutfreund et al., "Quantitative Parameters for Amino Acid-Base Interaction: Implication for Prediction of Protein-DNA Binding Sites," *Nuc. Acids Res.* 26(10):2306-2312 (1998).

Margolin et al., "Kruppel-Associated Boxes are Potent Transcriptional Repression Domains," *PNAS* 91:4509-4513 (1994).

Miller et al., "Construction and Properties of Retrovirus Packaging Cells Based on Gibbon Ape Leukemia Virus," *Journal of Virology* 65(5):2220-2224 (1991).

Mizushima et al., "pEF-BOS, a Powerful Mammilian Expression Vector," *Nuc. Acids. Res.* 18(17):5322 (1990).

Nakagama et al., "Sequence and Structural Requirements for High-Affinity DNA Binding by the WT1 Gene Product," *Molecular and Cellular Biology* 15(3):1489-1498 (1995).

Nardelli et al., "Zinc Finger-DNA Recognition: Analysis of Base Specificity by Site-Directed Mutagenesis," *Nucleic Acids Research* 20(16):4137-4144 (1992).

Nardelli et al., "Base Sequence Discrimination by Zinc-Finger DNA-Binding Domians," *Nature* 349:175-178 (1991).

Nekludova et al., "Distinctive DNA Conformation With Enlarged Major Groove is Found in Zn-Finger-DNA and Other Protein-DNA Complexes," *PNAS* 91:6948-6952 (1994).

Orkin et al., "Report and Recommendations of the Panel to Assess the NIH Investment in Research on Gene Therapy," (1995).

Pabo et al., "Systematic Analysis of Possible Hydrogen Bonds between Amino Acid Side Chains and B-form DNA," *J. Biomolecular Struct. Dynamic* 1:1039-1049 (1983).

Pabo et al., "Protein-DNA Recognition," *Ann. Rev. Biochem.* 53:293-321 (1984).

Pabo, C. O., "Transcription Factors: Structural Families and Principals of DNA Recognition," *Ann. Rev. Biochem.* 61: 1053-1095 (1992).

Pavletich et al., "Crystal Structure of a Five-Finger GLI-DNA Complex: New Perspectives on Zinc Fingers," *Science*, 261:1701-1707 (1993).

Pavletich et al., "Zinc Finger-DNA Recognition: Crystal Structure of a Zif268-DNA Complex at 2.1 A," *Science* 252:809-817 (1991).

Pengue et al., "Repression of Transcriptional Activity at a Distance by the Evolutionarily Conserved KRAB Domain Present in a Subfamily of Zinc Finger Proteins," *Nuc. Acids Res.* 22(15):2908-2914 (1994).

Pengue et al., "Transcriptional Silencing of Human Immunodeficiency Virus Type I Long Terminal Repeat-Driven Gene Expression by the Kruppel-Associated Box Repressor Domain Targeted to the Transactivating Response Element," *J. Virology* 69(10):6577-6580 (1995).

Pengue et al., "Kruppel-Associated Box-Mediated Repression of RNA Polymerase 11 Promoters is Influenced by the Arrangement of Basal Promoter Elements," *PNAS* 93:1015-1020 (1996).

Pomerantz et al., "Analysis of Homeodomain Function by Structure-Based Design of a Transcription Factor," *PNAS* 92:9752-9756 (1995).

Pomerantz et al., "Structure-Based Design of Transcription Factors," *Science* 267:93-96 (1995).

Pomerantz et al., "Structure-Based Design of a Dimeric Zinc Finger Protein," *Biochemistry* 37(4):965-970 (1998).

Qian et al., "Two-Dimensional NMR Studies of the Zinc Finger Motif:. Solution Structures and Dynamics of Mutant ZFY Domains Containing Aromatic Substitutions in the Hydrophobic Core," *Biochemistry* 31:7463-7476 (1992).

Quigley et al., "Complete Androgen Insensitivity Due to Deletion of Exon C of the Androgen Receptor Gene Highlights the Functional Importance of the Second Zinc Finger of the Androgen Receptor In Vivo," *Molecular Endocrinology* 6(7):1103-1112 (1992).

Rauscher et al., "Binding of the Wilms' Tumor Locus Zinc Finger Protein to the EGR-I Consensus Sequence," *Science* 250:1259-1262 (1990).

Ray et al., "Repressor to Activator Switch by Mutations in the First Zn Finger of the Glucocorticoid Receptor: Is Direct DNA Binding Necessary?," *PNAS* 88:7086-7090 (1991).

Rebar et al., "Phage Display Methods for Selecting Zinc Finger Proteins with Novel DNA-Binding Specificities," *Methods in Enzymology* 267:129-149 (1996).

Rebar et al., "Zinc Finger Phage: Affinity Selection of Fingers With New DNA-Binding Specifities," *Science* 263:671-673 (1994).

Reith et al., "Cloning of the Major Histocompatibility Complex Class II Promoter Binding Protein Affected in a Hereditary Defect in Class II Gene Regulation," *PNAS* 86:4200-4204 (1989).

Rhodes et al., "Zinc Fingers: They Play a Key Part of Regulating the Activity of Genes in Many Species, From Yeast to Humans. Fewer Than 10 Years Ago No One Knew They Existed." *Scientifc American* 268:56-65 (1993).

Rice et al., "Inhibitors of HIV Nucleocapsid Protein Zinc Fingers as Candidates for the Treatment of AIDS," *Science*. 270:1194-1197 (1995).

Rivera et al., "A Humanized System for Pharmacologic Control of Gene Expression," *Nature Medicine* 2(9):10281032 (1996).

Rollins et al., "Role of TFIIIA Zinc Fingers In vivo: Analysis of Single-Finger Function in Developing *Xenopus* Embryos," *Molecular Cellular Biology* 13(8):4776-4783 (1993).

Saleh et al., "A Novel Zinc Finger Gene on Human Chromosome 1 qter That is Alternatively Spliced in Human Tissues and Cell Lines," *American Journal of Human Genetics* 52:192-203 (1993).

Samulski et al., "Helper-Free Stocks of Recombinant Adeno-Associated Viruses: Normal Integration Does Not Require Viral Gene Expression," *Journal of Virology* 63(9):3822-3828 (1989).

Shi et al., "Specific DNA-RNA Hybrid Binding by Zinc Finger Proteins," *Science* 268:282-284 (1995).

Shi et al., "DNA Unwinding Induced by Zinc Finger Protein Binding," *Biochemistry* 35:3845-3848 (1996).

Shi et al., "A Direct Comparison of the Properties of Nnatural and Designed Finger Proteins," *Chem. & Biol.* 2(2):83-89 (1995).

Singh et al., "Molecular Cloning of an Enhancer Binding Protein: Isolation by Screening of an Expression Library with a Recognition Site DNA," *Cell* 52:415-423 (1988).

Skerka et al., "Coordinate Expression and Distinct DNA-Binding Characteristics of the Four EGR-Zinc Finger Proteins in Jurkat T Lymphocytes," *Immunobiology* 198:179-191 (1997).

Sommerfelt et al., "Receptor Interference Groups of 20 Retroviruses Plating on Human Cells," *Virology* 176:58-59 (1990).

South et al., "The Nucleocapsid Protein Isolated from HIV-1 Particles Binds Zinc and Forms Retroviral-Type Zinc Fingers," *Biochemistry* 29:7786-7789 (1990).

Spengler et al., "Regulation of Apoptosis and Cell Cycle Arrest by ZZC1, A Novel Zincfinger Protein Expressed in the Pituitary Gland and the Brain," *EMBO Journal 6B, Oxford University Press, Surrey* 16(10):2814-2825 (1997).

Suzuki et al., "Stereochemical Basis of DNA Recognition by Zn Fingers," *Nuc. Acids Res.* 22(16):3397-3405 (1994).

Suzuki et al. "DNA Recognition Code of Transcription Factors in the Helix-turn-Helix, Probe Helix, Hormone Receptor, and Zinc Finger Families," *PNAS* 91:12357-12361 (1994).

Swirnoff et al., "DNA-Binding Specificity of NGFI-A and Related Zinc Finger Transcription Factors," *Mol. Cell. Biol.* 15(4):2275-2287 (1995).

Taylor et al., "Designing Zinc-Finger ADRI Mutants with Altered Specificity of DNA Binding to T in UASI Sequences," *Biochemistry* 34:3222-3230 (1995).

Thiesen et al., "Determination of DNA Binding Specificities of Mutated Zinc Finger Domains," *FEBS Letters* 283(I):23-26 (1991).

Thiesen et al., "Amino Acid Substitutions in the SP1 Zinc Finger Domain Alter the DNA Binding Affinity to Cognate SP1 Target Site," *Biochem. Biophys. Res. Communications* 175(I):333-338 (1991).

Thiesen, H.J., "From Repression Domains to Designer Zinc Finger Proteins: A Novel Strategy for Intracellular Immunization Against HIV," *Gene Expression* 5:229-243 (1996).

Thukral et al., "Localization of a Minimal Binding Domain and Activation Regions in Yeast Regulatory Protein ADRI1," *Molecular Cellular Biology* 9(6):2360-2369 (1989).

Thukral et al., "Two Monomers of Yeast Transcription Factor ADR1 Bind a Paldromic Sequence Symmetrically to Activate *ADH2* Expression," *Molecular Cellular Biol.* 11(3):1566-1577 (1991).

Thukral et al., "Alanine Scanning Site-Directed Mutagenesis of the Zinc Fingers of Transcription Factor ADR1: Residues that Contact DNA and that Transactivate," *PNAS* 88:9188-9192 (1991) + correction page.

Thukral et al., "Mutations in the Zinc Fingers of ADR1 That Changes the Specificity of DNA Binding and Transactivation," *Mol. Cell Biol.* 12(6):2794-2792 (1992).

Tratschin et al., "Adeno-Associated Virus Vector for High-Frequency Integration, Expression, and Rescue of Genes in Mammalian Cells," *Molecular and Cellular Biology* 5(11):3251-3260 (1985).

Tratschin et al., "A Human Parvovirus, Adeno-Associated Virus, as a Eucaryotic Vector: Transient Expression and Encapsidation of the Procaryotic Gene for Chloramphenicol Acetyltransferase," *Molecular and Cellualr Biology* 4(10):2072-2081 (1984).

Vortkamp et al., "Identification of Optimized Target Sequences for the GL13 Zinc Finger Protein," *DNA Cell Biol.* 14(7):629-634 (1995).

Wang et al., "Dimerization of Zinc Fingers Mediated by Peptides Evolved in vitro from Random Sequences," *Proc. Natl. Acad. Sci. U.S.A.* 96:9568-9573 (1999).

Webster et al., "Conversion of the E1A Cys4 Zinc Finger to a Nonfunctional His2, Cys2 Zinc Finger by a Single Point Mutation," *PNAS* 88:9989-9993 (1991).

Whyatt et al., "The Two Zinc Finger-Like Domains of GATA-1 Have Different DNA Binding Specificities," *EMBO J.* 12(13):4993-5005 (1993).

Wilson et al., "In Vivo Mutational Analysis of the NGFI-A Zinc Fingers," *J. Biol. Chem.* 267(6):3718-3724 (1992).

Wilson et al., "Formation of Infectious Hybrid Virions with Gibbon Ape Leukemia Virus and Human T-Cell Leukemia Virus Tretoviral Envelope Clycoproteins and the gag and pol Proteins of Moloney Murine Leukemia Virus," Journal of Virology 63(5):2374-2378 (1998).

Witzgall et al., "The Kruppel-Associated Box-A (KRAB-A) Domain of Zinc Finger Proteins Mediates Transcriptional Repression," *PNAS* 91:4514-4518 (1994).

Wolfe et al., "Analysis of Zinc Fingers Optimized *Via* Phage Display: Evaluating the Utility of a Recognition Code," *J. Mol. Biol.* 285:1917-1934 (1999).

Wright et al., "Expression of a Zinc Finger Gene in HTLV-1 and HTLV-II Transformed Cells," *Science* 248:588-591 (1990).

Wu et al., "Building Zinc Fingers by Selection: Toward a Therapeutic Application," *Proc. Natl. Acad. Sci. U.S.A.* 92:344-348 (1995).

Yang et al., "Surface Plasmon Resonance Based Kinetic Studies of Zinf Finger-DNA Interaction," *J. Immunol. Methods* 183:175-182 (1995).

Yu et al., "A Hairpin Ribozyme Inhibits Expression of Diverse Strains of Human Immunodeficiency Virus Type 1," *PNAS* 90:6340-6344 (1993).

Zhang et al., "Synthetic Zinc Finger Transcription Factor Action at an Endogenous Chromosomal Site. Activation of the Human Erythropoietin Gene," *Journal of Biological Chemistry* 275(43):33850-33860 (2000).

RANDOMIZED LIBRARIES OF ZINC FINGER PROTEINS

CROSS-REFERENCES TO RELATED APPLICATIONS

This application is a continuation of U.S. Ser. No. 09/731,558, filed Dec. 6, 2000, now U.S. Pat. No. 6,503,717; which is a continuation-in-part of U.S. Ser. No. 09/456,100, filed Dec. 6, 1999, now abandoned. The disclosures of both of these applications are hereby incorporated by reference in their entireties for all purposes.

STATEMENT AS TO RIGHTS TO INVENTIONS MADE UNDER FEDERALLY SPONSORED RESEARCH AND DEVELOPMENT

Not applicable.

FIELD OF THE INVENTION

The present invention relates to methods of using libraries of randomized zinc finger proteins to identify genes associated with selected phenotypes.

BACKGROUND OF THE INVENTION

A. Using libraries to identify genes associated with a selected phenotype

Identification of gene function is a critical step in the selection of new molecular targets for drug discovery, gene therapy, clinical diagnostics, agrochemical discovery, engineering of transgenic plants, e.g., with novel resistance traits or enhanced nutritional characteristics, and genetic engineering of prokaryotes and higher organisms for the production of industrial chemicals, biochemicals, and chemical intermediates. Historically, library screening methods have been used to screen large numbers of uncharacterized genes to identify a gene or genes associated with a particular phenotype, e.g., hybridization screening of nucleic acid libraries, antibody screening of expression libraries, and phenotypic screening of libraries.

For example, molecular markers that ca-segregate with a disease trait in a segment of patients can be used as nucleic acid probes to identify, in a library, the gene associated with the disease. In another method, differential gene expression in cells and nucleic acid subtraction can be used to identify and clone genes associated with a phenotype in the test cells, where the control cells do not display the phenotype. However, these methods are laborious because the screening step relies heavily on conventional nucleic acid cloning and sequencing techniques. Development of high throughput screening assays using these methods would therefore be cumbersome.

An example of phenotypic screening of libraries is discovery of transforming oncogenes (see, e.g., Goldfarb et al., *Nature* 296:404 (1982)). Oncogenic transformation can be observed in NIH 3T3 cells by assaying for loss of contact inhibition and foci formation. cDNA expression libraries from transformed cells are introduced into untransformed cells, and the cells were examined for foci formation. The gene associated with transformation is isolated by clonal propagation and rescue of the expression vector. Unfortunately, this method is limited by phenotype and can only be used to assay for transdominant genes.

Advances in the field of high throughput screening have increased the cell types and phenotypes that can be investigated using library screening methods. Viral vectors such as retroviral, adenoviral, and adenoviral associated vectors have been developed for efficient nucleic acid delivery to cells (see, e.g., U.S. Pat. No. 5,173,414; Tratschin et al., *Mol. Cell. Biol.* 5:3251-3260 (1985); Tratschin, et al., *Mol. Cell. Biol.* 4:2072-2081 (1984); Hermonat & Muzyczka, *Proc. Nat'l Acad. Sci. USA* 81:6466-6470 (1984); and Samulski et al., *J. Virol.* 63:03822-3828 (1989); Buchscher et al., *J. Virol.* 66:2731-2739 (1992); Johann et al., *J. Virol.* 66:1635-1640 (1992); Sommerfelt et al., *Virol.* 176:58-59 (1990); Wilson et al., *J. Virol.* 63:2374-2378 (1989); Miller et al., *J. Virol.* 65:2220-2224 (1991); and PCT/US94/05700). Cells can be phenotypically analyzed either one at a time, using flow cytometry, or in arrayed clonal populations, using liquid handling robots. These techniques allow a sufficient number of library members to be tested for a wide range of potential phenotypes.

Currently, libraries of random molecules are being used with phenotypic screening for the discovery of genes associated with a particular phenotype. For example, random peptide or protein expression libraries are being used to block specific protein-protein interactions and produce a particular phenotype (see, e.g., Caponigro et al., *Proc. Nat'l Acad. Sci USA* 95:7508-7513 (1998); WO 97/27213; and WO 97 27212). In another method, random antisense nucleic acids or ribozymes are used to inactivate a gene and produce a desired phenotype (see, e.g., WO 99/41371 and Hannon et al., *Science* 283:1125-1126 (1999)).

The main shortcoming of these methods is the inherent inefficiency of the random molecules, which vastly increases the size of the library to be screened. Even with a known target nucleic acid or protein, literally hundreds of antisense, ribozyme, or peptide molecules must be empirically tested before identifying one that will inhibit gene expression or protein-protein interactions. Since the random library must be enormous to produce sufficient numbers of active molecules, huge numbers of cells must be screened for phenotypic changes. For unknown gene and protein targets, the rarity of effective, bioactive peptides, antisense molecules, or ribozyme molecules imposes significant constraints on high throughput screening assays. Furthermore, these methods can be used only for inhibition of gene expression, but not for activation of gene expression. This feature limits identification of gene function to phenotypes present only in the absence of gene expression.

Therefore, efficient high throughput library screening methods allowing random inhibition or activation of uncharacterized genes would be of great utility to the scientific community. These methods would find widespread use in academic laboratories, pharmaceutical companies, genomics companies, agricultural companies, chemical companies, and in the biotechnology industry.

B. Zinc finger proteins as transcriptional regulators

Zinc finger proteins ("ZFPs") are proteins that bind to DNA in a sequence-specific manner and are typically involved in transcription regulation. Zinc finger proteins are widespread in eukaryotic cells. An exemplary motif characterizing one class of these proteins (the $Cys_2His_2$ class) is -Cys-$(X)_{2-4}$-Cys-$(X)_{12}$-His-$(X)_{3-5}$-His (where X is any amino acid). A single finger domain is about 30 amino acids in length and several structural studies have demonstrated that it contains an alpha helix containing the two invariant histidine residues co-ordinated through zinc with the two cysteines of a single beta turn. To date, over 10,000 zinc finger sequences have been identified in several thousand known or putative transcription factors. Zinc finger proteins are involved not only in DNA-recognition, but also in RNA binding and protein-protein binding. Current estimates are that this class of molecules will constitute the products of about 2% of all human genes.

The X-ray crystal structure of Zif268, a three-finger domain from a murine transcription factor, has been solved in complex with its cognate DNA-sequence and shows that each finger can be superimposed on the next by a periodic rotation and translation of the finger along the main DNA axis. The structure suggests that each finger interacts independently with DNA over 3 base-pair intervals, with side-chains at positions −1, 2, 3 and 6 on each recognition helix making contacts with respective DNA triplet sub-site.

The structure of the Zif268-DNA complex also suggested that the DNA sequence specificity of a zinc finger protein could be altered by making amino acid substitutions at the four helix positions (−1, 2, 3 and 6) on a zinc finger recognition helix, using, e.g., phage display experiments (see, e.g., Rebar et al., *Science* 263:671-673 (1994); Jamieson et al., *Biochemistry* 33:5689-5695 (1994); Choo et al., *Proc. Natl. Acad. Sci. U.S.A.* 91:11163-11167 (1994); Greisman & Pabo, *Science* 275:657-661 (1997)). For example, combinatorial libraries were constructed with zinc finger proteins randomized in either the first or middle finger. The randomized zinc finger proteins were then isolated with altered target sites in which the appropriate DNA sub-site was replaced by an altered DNA triplet. Correlation between the nature of introduced mutations and the resulting alteration in binding specificity gave rise to a set of substitution rules for rational design of zinc finger proteins with altered binding specificity. These experiments thus demonstrated that randomized zinc finger proteins could be made, which demonstrated altered target sequence specificity.

Recombinant zinc finger proteins, often combined with a heterologous transcriptional activator or repressor domain, have also shown efficient transcriptional regulation of transiently expressed reporter genes in cultured cells (see, e.g., Pomerantz et al., *Science* 267:93-96 (1995); Liu et al., *Proc. Natl. Acad. Sci. U.S.A.* 94:5525-5530 1997); and Beerli et al., *Proc. Natl. Acad. Sci. U.S.A.* 95:14628-14633 (1998)). For example, Pomerantz et al., *Science* 267:93-96 (1995) designed a novel DNA binding protein by fusing two fingers from Zif268 with a homeodomain from October 1. The hybrid protein was then fused with either a transcriptional activator or repressor domain for expression as a chimeric protein. The chimeric protein was reported to bind a target site representing a hybrid of the subsites of its two components. The chimeric DNA binding protein also activated or repressed expression of a reporter luciferase gene having a target site.

Liu et al., *Proc. Natl. Acad. Sci. U.S.A.* 94:5525-5530 (1997) constructed a composite zinc finger protein by using a peptide spacer to link two component zinc finger proteins, each having three fingers. The composite protein was then further linked to transcriptional activation or repression domains. The resulting chimeric protein bound to a target site formed from the target segments bound by the two component zinc finger proteins. The chimeric zinc finger protein activated or repressed transcription of a reporter gene having the target site.

Beerli et al., *Proc. Natl. Acad. Sci. U.S.A.* 95:14628-1,4633 (1998) constructed a chimeric six finger zinc finger protein fused to either a KRAB, ERD, or SID transcriptional repressor domain, or the VP16 or VP64 transcriptional activation domain. This chimeric zinc finger protein was designed to recognize an 18 bp target site in the 5' untranslated region of the human erbB-2 gene. This construct both activated and repressed a transiently expressed reporter luciferase construct linked to the erbB-2 promoter.

In addition, a recombinant zinc finger protein was reported to repress expression of an integrated plasmid construct encoding a bcr-abl oncogene (Choo et al., *Nature* 372:642-645 (1994)). Phage display was used to select a variant zinc finger protein that bound to the selected target segment. The variant zinc finger protein thus isolated was then reported to repress expression of a stably transfected bcr-abl construct in a cell line. To date, these zinc finger protein methods have focused on regulation of either single, transiently expressed, known genes, or on regulation of single, known exogenous genes that have been integrated into the genome.

SUMMARY OF THE INVENTION

The present application therefore provides for the first time methods of using libraries of randomized zinc finger proteins to screen large numbers of genes, for identifying a gene or genes associated with a selected phenotype. These libraries of randomized zinc finger DNA binding proteins have the ability to regulate gene expression with high efficiency and specificity. Because zinc finger proteins provide a reliable, efficient means for regulating gene expression, the libraries of the invention typically have no more than about $10^6$ to about $10^7$ members. This manageable library size means that libraries of randomized zinc finger proteins can be efficiently used in high throughput applications to quickly and reliably identify genes of interest that are associated with any given phenotype.

In one aspect, the present invention provides a method of identifying a gene or genes associated with a selected phenotype, the method comprising the steps of: (a) providing a nucleic acid library comprising nucleotide sequences that encode partially randomized zinc finger proteins; (b) transducing cells with expression vectors, each comprising a nucleotide sequence from the library; (c) culturing the cells so that zinc finger proteins are expressed in the cells, wherein the zinc finger proteins modulate gene expression in at least some of the cells; (d) assaying the cells for a selected phenotype and determining whether or not the cells exhibit the selected phenotype; and (e) identifying, in cells that exhibit the selected phenotype, the gene or genes whose expression is modulated by expression of a zinc finger protein, wherein the gene so identified is associated with the selected phenotype.

In one embodiment, the zinc finger protein has three, four, or five fingers. In another embodiment, the library is made by finger grafting, DNA shuffling, or codon doping. In another embodiment, the library comprises no more than about $10^6$ clones, no more than about $10^7$ clones, or no more than about $10^8$ clones.

In one embodiment, the cells are physically separated, individual pools of cells and each individual pool of cells is transduced with an expression vector comprising a nucleotide sequence from the library. In another embodiment, the physical separation of the pools of cells is accomplished by placing each pool of cells in a separate well of a 96, 384, or 1536 well plate. In another embodiment, the cells are assayed for the selected phenotype using liquid handling robots. In another embodiment, the cells are pooled together and transduced in a batch. In another embodiment, the cells are assayed for the selected phenotype using flow cytometry. In one embodiment, the cells are selected from the group consisting of animal cells, plant cells, bacterial cells, protozoal cells, mammalian cells, human cells, or fungal cells.

In one embodiment, zinc finger proteins are fusion proteins comprising one or two regulatory domains, e.g., a transcriptional repressor, a methyl transferase, a transcriptional activator, a histone acetyltransferase, and a histone deacetylase. In another embodiment, the regulatory domain is VP16 or KRAB. In another embodiment, the zinc finger proteins comprise a Zif268 backbone.

In one embodiment, modulation of gene expression is repression of gene expression. In another embodiment, modulation of gene expression is activation of gene expression. In one embodiment, expression of the zinc finger proteins is controlled by administration of a small molecule, e.g., tetracycline.

In one embodiment, the expression vectors are a viral vector, e.g., a retroviral expression vector, a lentiviral expression vector, an adenoviral expression vector, or an AAV expression vector.

In one embodiment, the selected phenotype is related to cancer, nephritis, prostate hypertrophy, hematopoiesis, osteoporosis, obesity, cardiovascular disease, or diabetes. In one embodiment, genes that are suspected of being associated with the selected phenotype are identified by comparing differential gene expression patterns in the presence and absence of expression of the zinc finger protein. In another embodiment, differential gene expression patterns are compared using an oligonucleotide array. In another embodiment, genes that are suspected of being associated with the selected phenotype are identified by using zinc finger proteins from the library of randomized zinc finger proteins to probe YAC or BAC clones. In another embodiment, genes that are suspected of being associated with the selected phenotype are identified by scanning genomic sequences for target sequences recognized by zinc finger proteins from the library of randomized zinc finger proteins. In another embodiment, genes that are suspected of being associated with the selected phenotype are identified by cross-linking the zinc finger protein to DNA with which it is associated, followed by immunoprecipitation of the zinc finger protein and sequencing of the DNA.

DETAILED DESCRIPTION OF THE INVENTION

Figure 1:
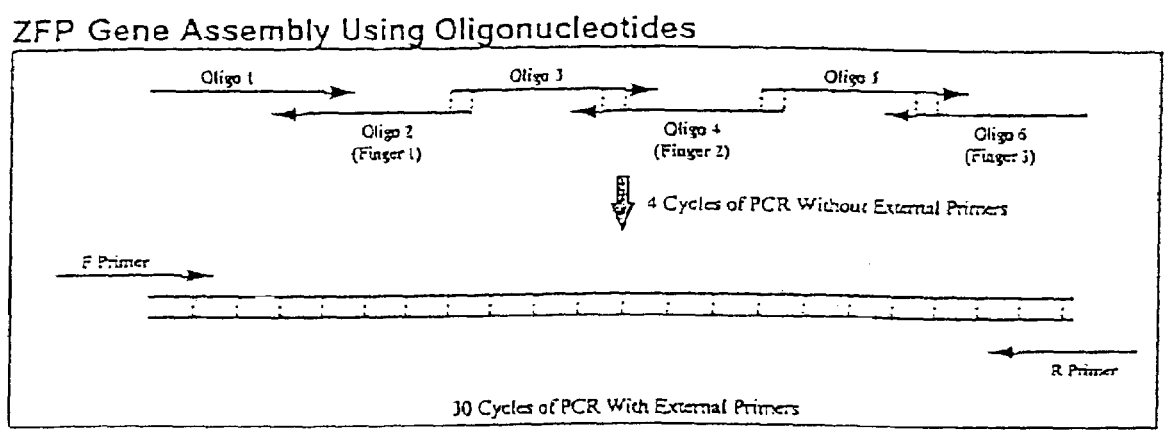
FIG. 1 shows a zinc finger protein gene assembly using PCR.
Figure 2:
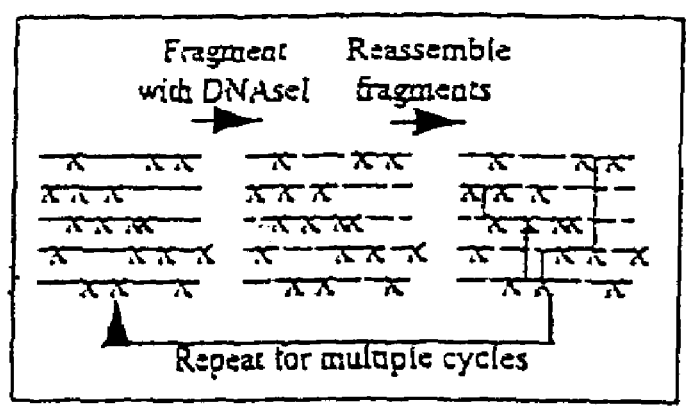
FIG. 2 shows a diagram of making random zinc finger proteins with DNA shuffling.

As described herein, the present invention provides libraries of randomized zinc finger proteins used in -screening assays to identify a gene or genes associated with a selected phenotype. These libraries of randomized zinc finger proteins can be readily used to either up- or down-regulate gene expression. No target DNA sequence information is required to create a random DNA binding domain. This feature makes the zinc finger protein technology ideal for screening for genes that are associated with a desired phenotype. One can simply create a library of randomized zinc finger-based DNA binding domains, create chimeric up and down-regulating transcription factors and test the effect of up or down-regulation on the phenotype under study (transformation, response to a cytokine etc.) by switching the genes on or off in any model system.

Additionally, greater experimental control can be imparted by zinc finger proteins than can be achieved by more conventional methods such as antisense, ribozyme, and peptide applications. This control is available because the expression and/or function of an engineered zinc finger protein can be placed under small molecule control. Examples of this approach are provided, e.g., by the Tet-On system, the ecdysone-regulated system, and the RU-486 system (see, e.g., Gossen & Bujard, $Proc. Natl. Acad. Sci. U.S.A.$ 89:5547 (1992); Oligino et al., $Gene Ther.$ 5:491-496 (1998); Wang et al., $Gene Ther.$ 4:432-441 (1997); Neering et al., $Blood$ 88:1147-1155 (1996); and Rendahl et al., $Nat. Biotechnol.$ 16:757-761 (1998)).

In the present invention, a nucleic acid library of about no more than $10^6$ to $10^7$ partially randomized zinc finger proteins is made, using techniques such as codon doping, gene shuffling, and finger grafting. Often, a three-fingered zinc protein is used in the methods of the invention. Cells are then transfected with the library for expression of a zinc finger protein clone. Preferably, the zinc finger proteins are introduced into the cell using viral expression vectors, e.g., retroviral or adenoviral-based vectors. The cells are then assayed for changes in the phenotype of choice. Cells can be assayed one by one, using techniques such as flow cytometry, or in pools of arrayed clonal populations, using liquid handling robots (see Example section, below).

Examples of assay systems for changes in phenotype include, e.g., transformation assays, e.g., changes in proliferation, anchorage dependence, growth factor dependence, foci formation, and growth in soft agar; apoptosis assays, e.g., DNA laddering and cell death, expression of genes involved in apoptosis; signal transduction assays, e.g., changes in intracellular calcium, cAMP, cGMP, IP3, changes in hormone and neurotransmitter release; receptor assays, e.g., estrogen receptor and cell growth; growth factor assays, e.g., EPO, hypoxia and erythrocyte colony forming units assays; enzyme production assays, e.g., FAD-2 induced oil desaturation; pathogen resistance assays, e.g., insect, bacterial, and viral resistance assays; chemical production assays, e.g., penicillin production; transcription assays, e.g., reporter gene assays; and protein production assays, e.g., VEGF ELISAs.

Those cells exhibiting an altered phenotype are selected for further study, in which the genes associated with the change in phenotype are identified and isolated. The genes are identified and isolated, e.g., using differential gene expression analysis with microarrays; reverse genetics; e.g., identification of genes using zinc finger proteins to probe YAC or BAC clones and using zinc finger proteins to scan genomic sequences; subtractive hybridization; differential cDNA cloning frequencies, subtractive hybridization; by cloning ESTs from cells of interest; by identifying genes that are lethal upon knockout; by identifying genes that are up- or down-regulated in response to a particular developmental or cellular event or stimuli; by identifying genes that are up- or down-regulated in certain disease and pathogenic states; by identifying mutations and RFLPs; by identifying genes associated with regions of chromosomes known to be involved in inherited diseases; by identifying genes that are temporally regulated, e.g., in a pathogenic organism; differences based on SNPs, etc.

In one embodiment, the zinc finger protein is linked to at least one or more regulatory domains, described in detail below. Preferred regulatory domains include transcription factor repressor or activator domains such as KRAB and VP 16, co-repressor and co-activator domains, DNA methyltransferases, histone acetyltransferases, histone deacetylases, and endonucleases such as Fok1. For repression of gene expression, often simple steric hindrance of transcription initiation is sufficient.

Such assays for candidate genes allow for discovery of novel human and veterinary therapeutic and diagnostic applications, including the discovery of novel drugs, for, e.g., treatment of genetic diseases, cancer, fungal, protozoal, bacterial, and viral infection, ischemia, vascular disease, arthritis, immunological disorders, etc. In addition, the methods of the invention can be used in the agricultural industry for the identification of commercially relevant plant genes, and can be used to engineer bacteria and other organisms to produce industrial chemicals and pharmaceuticals.

Definitions

As used herein, the following terms have the meanings ascribed to them unless specified otherwise.

"Partially randomized" zinc finger proteins refers to a zinc finger protein where at least some of the amino acids of any individual finger are generated randomly and are not preselected (e.g., the four critical amino acids of finger 1), or wherein at least one finger or part of a finger from a known zinc finger protein is randomly combined with another heterologous finger or part of a finger from a known zinc finger protein. Typically, a standard zinc finger protein backbone from a mammalian zinc finger protein such as SP1 or Zif268 is used to make the partially random protein, with the fingers either partially or fully randomized via random codon selection. In some cases the codons are partially randomized, e.g., to eliminate termination codons (see Table 2, below). Partially random zinc finger proteins include fully randomized zinc finger proteins. In one embodiment, amino acids −1, 2, 3, and 6 of a finger are randomly selected.

A "gene associated with a selected phenotype" refers to a cellular, viral, bacterial, protozoal, fungal, animal, plant, episomal, chloroplastic, or mitochondrial gene, where modulation of gene expression using a randomized zinc finger protein causes a change in the selected phenotype. This term also refers to a microbial or viral gene that is part of a naturally occurring microbial or viral genome in a microbially or virally infected cell. The microbial or viral genome can be extrachromosomal or integrated into the host chromosome. This term also encompasses endogenous and exogenous genes, as well as cellular genes that are identified as expressed sequence tags ("ESTs"). An assay of choice is used to identify genes associated with a selected phenotype upon regulation of gene expression with a zinc finger protein. The genes are typically identified via methods such as gene expression microarrays, differential cDNA cloning frequencies, subtractive hybridization and differential display methods. The genes associated with a selected phenotype are then subjected to target validation using engineered zinc finger proteins (see, e.g., co-owned U.S. Pat. No. 6,599,692).

A "selected phenotype" refers to any phenotype, e.g., any observable characteristic such as a physical, chemical, or functional effect that can be measured in an assay such as changes in cell growth, proliferation, morphology, enzyme function, signal transduction, expression patterns, downstream expression patterns, reporter gene activation, hormone release, growth factor release, neurotransmitter release, ligand binding, apoptosis, and product formation. Such assays include, e.g., transformation assays, e.g., changes in proliferation, anchorage dependence, growth factor dependence, foci formation, and growth in soft agar; apoptosis assays, eg., DNA laddering and cell death, expression of genes involved in apoptosis; signal transduction assays, e.g., changes in intracellular calcium, cAMP, cGMP, IP3, changes in hormone and neurotransmitter release; receptor assays, e.g., estrogen receptor and cell growth; growth factor assays, e.g., EPO, hypoxia and erythrocyte colony forming units assays; enzyme production assays, e.g., FAD-2 induced oil desaturation; pathogen resistance assays, e.g., insect, bacterial, and viral resistance assays; chemical production assays, e.g., penicillin production; transcription assays, e.g., reporter gene assays; and protein production assays, e.g., VEGF ELISAs.

The term "zinc finger protein" or "ZFP" refers to a protein having DNA binding domains that are stabilized by zinc. The individual DNA binding domains are typically referred to as "fingers" A zinc finger protein has at least one finger, typically two fingers, three fingers, four fingers, five fingers, or six fingers or more. Each finger binds from two to four base pairs of DNA, typically three or four base pairs of DNA. A zinc finger protein binds to a nucleic acid sequence called a target site or target segment. Each finger typically comprises an approximately 30 amino acid, zinc-coordinating, DNA-binding subdomain. An exemplary motif characterizing one class of these proteins ($Cys_2His_2$ class) is -Cys-$(X)_{2-4}$-Cys-$(X)_{12}$-His-$(X)_{3-5}$-His (where X is any amino acid). Studies have demonstrated that a single zinc finger of this class consists of an alpha helix containing the two invariant histidine residues co-ordinated with zinc along with the two cysteine residues of a single beta turn (see, e.g., Berg & Shi, *Science* 271:1081-1085 (1996)).

A "target site" is the nucleic acid sequence recognized by a zinc finger protein. A single target site typically has about four to about ten or more base pairs. Typically, a two-fingered zinc finger protein recognizes a four to seven base pair target site, a three-fingered zinc finger protein recognizes a six to ten base pair target site, a six fingered zinc finger protein recognizes two adjacent nine to ten base pair target sites, and so on for proteins with more than six fingers. The target site is in any position that allows regulation of gene expression, e.g., adjacent to, up- or downstream of the transcription initiation site; proximal to an enhancer or other transcriptional regulation element such as a repressor (e.g., SP-1 binding sites, hypoxia response elements, nuclear receptor recognition elements, p53 binding sites, etc.), RNA polymerase pause sites; and intron/exon boundaries. The term "adjacent target sites" refers to non-overlapping target sites that are separated by zero to about 5 base pairs.

"$K_d$" refers to the dissociation constant for the compound, i.e., the concentration of a compound (e.g., a zinc finger protein) that gives half maximal binding of the compound to its target (i.e., half of the compound molecules are bound to the target) under given conditions (i.e., when [target]<<$K_d$), as measured using a given assay system (see, e.g., U.S. Pat. No. 5,789,538). The assay system used to measure the $K_d$ should be chosen so that it gives the most accurate measure of the actual $K_d$ of the zinc finger protein. Any assay system can be used, as long is it gives an accurate measurement of the actual $K_d$ of the zinc finger protein. In one embodiment, the $K_d$ for the zinc finger proteins of the invention is measured using an electrophoretic mobility shift assay ("EMSA"), as described herein. Unless an adjustment is made for zinc finger protein purity or activity, the $K_d$ calculations made using the methods described herein may result in an underestimate of the true $K_d$ of a given zinc finger protein. Optionally, the $K_d$ of a zinc finger protein used to modulate transcription of a candidate gene is less than about 100 nM, or less than about 75 nM, or less than about 50 nM, or less than about 25 nM.

"Administering" an expression vector, nucleic acid, zinc finger protein, or a delivery vehicle to a cell comprises transducing, transfecting, electroporating, translocating, fusing, phagocytosing, or ballistic methods, etc., i.e., any means by which a protein or nucleic acid can be transported across a cell membrane and preferably into the nucleus of a cell, including administration of naked DNA.

A "delivery vehicle" refers to a compound, e.g., a liposome, toxin, or a membrane translocation polypeptide, which is used to administer a zinc finger protein. Delivery vehicles can also be used to administer nucleic acids encoding zinc finger proteins, e.g., a lipid:nucleic acid complex, an expression vector, a virus, and the like.

The terms "modulating expression" "inhibiting expression" and "activating expression" of a gene refer to the ability of a zinc finger protein to activate or inhibit transcription of a gene. Activation includes prevention of transcriptional inhibition (i.e., prevention of repression of gene expression) and inhibition includes prevention of transcriptional activation (i.e., prevention of gene activation).

"Activation of gene expression that prevents repression of gene expression" refers to the ability of a zinc finger protein to block the action of or prevent binding of a repressor molecule.

"Inhibition of gene expression that prevents gene activation" refers to the ability of a zinc finger protein to block the action of or prevent binding of an activator molecule.

Modulation can be assayed by determining any parameter that is indirectly or directly affected by the expression of the target gene. Such parameters include, e.g., changes in RNA or protein levels, changes in protein activity, changes in product levels, changes in downstream gene expression, changes in reporter gene transcription (luciferase, CAT, β-galactosidase, β-glucuronidase, GFP (see, e.g., Mistili & Spector, *Nature Biotechnology* 15:961-964 (1997)); changes in signal transduction, phosphorylation and dephosphorylation, receptor-ligand interactions, second messenger concentrations (e.g., cGMP, cAMP, IP3, and $Ca^{2+}$), and cell growth, etc., as described herein. These assays can be in vitro, in vivo, and ex vivo. Such functional effects can be measured by any means known to those skilled in the art, e.g., measurement of RNA or protein levels, measurement of RNA stability, identification of downstream or reporter gene expression, e.g., via chemiluminescence, fluorescence, fluorescent activated cell sorting ("FACS"), colorimetric reactions, antibody binding, inducible markers, ligand binding assays; changes in intracellular second messengers such as cGMP and inositol triphosphate (IP3); changes in intracellular calcium levels; cytokine release, and the like, as described herein.

To determine the level of gene expression modulation effected by a zinc finger protein, cells contacted with zinc finger proteins are compared to control cells, e.g., without the zinc finger protein or with a non-specific zinc finger protein, to examine the extent of inhibition or activation. Control samples are assigned a relative gene expression activity value of 100%. Modulation/inhibition of gene expression is achieved when the gene expression activity value relative to the control is about 80%, preferably 50% (i.e., 0.5× the activity of the control), more preferably 25%, more preferably 5-0%. Modulation/activation of gene expression is achieved when the gene expression activity value relative to the control is 110% , more preferably 150% (i.e., 1.5× the activity of the control), more preferably 200-500%, more preferably 1000-2000% or more.

A "transcriptional activator" and a "transcriptional repressor" refer to proteins or effector domains of proteins that have the ability to modulate transcription, as described above. Such proteins include, e.g., transcription factors and co-factors (e.g., KRAB, MAD, ERD, SID, nuclear factor kappa B subunit p65, early growth response factor 1, and nuclear hormone receptors, VP16, VP64), endonucleases, integrases, recombinases, methyltransferases, histone acetyltransferases, histone deacetylases etc. Activators and repressors include co-activators and co-repressors (see, e.g., Utley et al., *Nature* 394:498-502 (1998)).

A "regulatory domain" refers to a protein or a protein domain that has transcriptional modulation activity when tethered to a DNA binding domain, i.e., a zinc finger protein. Typically, a regulatory domain is covalently or non-covalently linked to a zinc finger protein to effect transcription modulation. Alternatively, a zinc finger protein can act alone, without a regulatory domain, to effect transcription modulation.

The term "heterologous" is a relative term, which when used with reference to portions of a nucleic acid indicates that the nucleic acid comprises two or more subsequences that are not found in the same relationship to each other in nature. For instance, a nucleic acid that is recombinantly produced typically has two or more sequences from unrelated genes synthetically arranged to make a new functional nucleic acid, e.g., a promoter from one source and a coding region from another source. The two nucleic acids are thus heterologous to each other in this context. When added to a cell, the recombinant nucleic acids would also be heterologous to the endogenous genes of the cell. Thus, in a chromosome, a heterologous nucleic acid would include an non-native (non-naturally occurring) nucleic acid that has integrated into the chromosome, or a non-native (non-naturally occurring) extrachromosomal nucleic acid.

Similarly, a heterologous protein indicates that the protein comprises two or more subsequences that are not found in the same relationship to each other in nature (e.g., a "fusion protein," where the two subsequences are encoded by a single nucleic acid sequence). See, e.g., Ausubel, supra, for an introduction to recombinant techniques.

The term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, for example, recombinant cells express genes that are not found within the native (naturally occurring) form of the cell or express a second copy of a native gene that is otherwise normally or abnormally expressed, under expressed or not expressed at all.

A "promoter" is defined as an array of nucleic acid control sequences that direct transcription. As used herein, a promoter typically includes necessary nucleic acid sequences near the start site of transcription, such as, in the case of certain RNA polymerase II type promoters, a TATA element, enhancer, CCAAT box, SP-1 site, etc. As used herein, a promoter also optionally includes distal enhancer or repressor elements, which can be located as much as several thousand base pairs from the start site of transcription. The promoters often have an element that is responsive to transactivation by a DNA-binding moiety such as a polypeptide, e.g., a nuclear receptor, Gal4, the lac repressor and the like.

A "constitutive" promoter is a promoter that is active under most enviromnental and developmental conditions. An "inducible" promoter is a promoter that is active under certain environmental or developmental conditions.

The term "operably linked" refers to a functional linkage between a nucleic acid expression control sequence (such as a promoter, or array of transcription factor binding sites) and a second nucleic acid sequence, wherein the expression control sequence directs transcription of the nucleic acid corresponding to the second sequence.

An "expression vector" is a nucleic acid construct, generated recombinantly or synthetically, with a series of specified nucleic acid elements that permit transcription of a particular nucleic acid in a host cell, and optionally, integration or replication of the expression vector in a host cell. The expression vector can be part of a plasmid, virus, or nucleic acid fragrnent, of viral or non-viral origin. Typically, the expression vector includes an "expression cassette," which comprises a nucleic acid to be transcribed operably linked to a promoter. The term expression vector also encompasses naked DNA operably linked to a promoter.

By "host cell" is meant a cell that contains a zinc finger protein or an expression vector or nucleic acid encoding a zinc finger protein. The host cell typically supports the replication and/or expression of the expression vector. Host cells may be prokaryotic cells such as $E.$ $coli$, or eukaryotic cells such as yeast, fungal, protozoal, higher plant, insect, or amphibian cells, or mammalian cells such as CHO, HeLa, 293, COS-1, and the like, e.g., cultured cells (in vitro), explants and primary cultures (in vitro and ex vivo), and cells in vivo.

"Nucleic acid" refers to deoxyribonucleotides or ribonucleotides and polymers thereof in either single- or double-stranded form. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, peptide-nucleic acids (PNAs).

Unless otherwise indicated, a particular nucleic acid sequence also implicitly encompasses conservatively modified variants thereof (e.g., degenerate codon substitutions) and complementary sequences, as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260:2605-2608 (1985); Rossolini et al., *Mol. Cell. Probes* 8:91-98 (1994)). The term nucleic acid is used interchangeably with gene, cDNA, mRNA, oligonucleotide, and polynucleotide.

The terms "polypeptide," "peptide" and "protein" are used interchangeably herein to refer to a polymer of amino acid residues. The terms also apply to amino acid polymers in which one or more amino acid residues is an artificial chemical mimetic of a corresponding naturally occurring amino acid, as well as to naturally occurring amino acid polymers and non-naturally occurring amino acid polymer.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

Amino acids may be referred to herein by either their commonly known three letter symbols or by the one-letter symbols recommended by the UUPAC-IUB Biochemical Nomenclature Commission. Nucleotides, likewise, may be referred to by their commonly accepted single-letter codes.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence.

As to amino acid sequences, one of skill will recognize that individual substitutions, deletions or additions to a nucleic acid, peptide, polypeptide, or protein sequence which alters, adds or deletes. a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The following eight groups each contain amino acids that are conservative substitutions for one another:
1) Alanine (A), Glycine (G);
2) Aspartic acid (D), Glutamic acid (E);
3). Asparagine (N), Glutamine (Q);
4) Arginine (R), Lysine (K);
5) Isoleucine (I), Leucine (L), Methionine (M), Valine (V);
6) Phenylalanine (F), Tyrosine (Y), Tryptophan (W);
7) Serine (S), Threonine (T); and
8) Cysteine (C), Methionine (M)

(see, e.g., Creighton, *Proteins* (1984)).

Making Libraries of Randomized Zinc Finger Proteins

Libraries of nucleic acids encoding randomized zinc finger proteins are generated for use in the methods of the invention. Typically, a backbone from any suitable $Cys_2His_2$ zinc finger protein, such as SP-1, SP-1C, or ZIF268, is used as the scaffold for the randomized zinc finger protein (see, e.g., Jacobs, *EMBO J.* 11:4507 (1992); Desjarlais & Berg, *Proc. Nat'l Acad. Sci. USA* 90:2256-2260 (1993)). A number of methods can then be used to generate libraries of nucleic acids encoding the randomized zinc finger proteins.

At least three different strategies can be used to make the random zinc finger protein libraries. The first method, called the finger or recognition helix grafting strategy, will typically have the least non-functional zinc finger proteins, and the recombination is limited only to the existing fingers. The second method, called the codon doping strategy, provides the most complete randomization scheme. The third method, called the gene shuffling strategy, will generate new variants for all fingers. In this method, however, the mutagenesis is not complete but is derived from only a limited number of parental zinc finger proteins. The three randomization schemes can be used herein to build the randomized zinc finger protein libraries and to test the libraries for DNA binding in vitro by using a phage display system (see Example section, below).

In one embodiment, the method used for zinc finger protein library construction is fingertip, or recognition helix grafting. Imagine a collection of 3-bp binding zinc finger protein helices that could be grafted together in any combination. Each unique multi-finger combination would recognize a different unique DNA sequence. The number of different fingers used and the number of fingers attached together can be varied in this method. In one embodiment, the number of different fingertips is about 10-14, optionally 12, and the number of fingers is 3-5, optionally 5, and a randomized zinc finger library size to screen preferably consists of 250,000+members.

There are about 140,000 genes in the human genome and the human genome has about $3 \times 10^9$ basepairs. In one embodiment, a library of five finger zinc finger proteins made with 20 different fingertips would recognize about 3,200,000 different 15 basepair sequences ($20^5$); a library made with 15 different fingertips would recognize about 759,375 different sequences; a library made with 13 fingertips would recognize about 371,293 different sequences; and a library made with 12 fingertips would recognize about 248,832. Using specific helices for all 64 triplets would be sufficient to recognize any and all 15 basepair sequences.

Considering both strands of the target genome, a 15 basepair sequence is expected to occur 0.6 times (($2.8 \times 10^8/4^{15}$)×2). In other words, of a random 5-finger library, at least 60 percent of the component zinc finger proteins are expected to affect the expression of a single gene. Considering the entire genome, a random 5-finger zinc finger protein is expected to have on average only 6 perfect binding sites.

On average, no more than one gene should be directly affected at a time by a component zinc finger protein, and only a handful of genomic binding sites need to be considered. In fact, the active zinc finger protein itself can be used to identify candidate genes either by sequence scanning or as probes to identify candidate genomic clones (i.e., from YAC or BAC clones).

In addition, any other suitable method known in the art can be used to construct nucleic acids encoding random zinc finger proteins, e.g., phage display, random mutagenesis, combinatorial libraries, affinity selection, PCR, cloning from cDNA or genomic libraries, synthetic construction and the like. (see, e.g., U.S. Pat. No. 5,786,538; Wu et al., *Proc. Nat'l Acad. Sci. USA* 92:344-348 (1995); Jamieson et al., *Biochemistry* 33:5689-5695 (1994); Rebar & Pabo, *Science* 263:671-673 (1994); Choo & Klug, *Proc. Nat'l Acad. Sci. USA* 91:11163-11167 (1994); Choo & Klug, *Proc. Nat'l Acad. Sci. USA* 91: 11168-11172 (1994); Desjarlais & Berg, *Proc. Nat'l Acad. Sci. USA* 90:2256-2260 (1993); Desjarlais & Berg, *Proc. Nat'l Acad. Sci. USA* 89:7345-7349 (1992); Pomerantz et al., *Science* 267:93-96 (1995); Pomerantz et al., *Proc. Nat'l Acad. Sci. USA* 92:9752-9756 (1995); and Liu et al., *Proc. Nat'l Acad. Sci. USA* 94:5525-5530 (1997); Greisman & Pabo, *Science* 275:657-661 (1997); Desjarlais & Berg, *Proc. Nat'l Acad. Sci. USA* 91:11-99-11103 (1994)).

Regulatory Domains

The zinc finger proteins of the invention can optionally be associated with regulatory domains for modulation of gene expression. The zinc finger protein can be covalently or non-covalently associated with one or more regulatory domains, alternatively two or more regulatory domains, with the two or more domains being two copies of the same domain, or two different domains. The regulatory domains can be covalently linked to the zinc finger protein, e.g., via an amino acid linker, as part of a fusion protein. The zinc finger proteins can also be associated with a regulatory domain via a non-covalent dimerization domain, e.g., a leucine zipper, a STAT protein N terminal domain, or an FK506 binding protein (see, e.g., O'Shea, *Science* 254: 539 (1991), Barahmand-Pour et al., *Curr. Top. Microbiol. Immunol.* 211:121-128 (1996); Klemm et al., *Annu. Rev. Immunol.* 16:569-592 (1998); Klemm et al., *Annu. Rev. Immunol.* 16:569-592 (1998); Ho et al., *Nature* 382:822-826 (1996); and Pomeranz et al., *Biochem.* 37:965 (1998)). The regulatory domain can be associated with the zinc finger protein at any suitable position, including the C- or N-terminus of the zinc finger protein.

Common regulatory domains for addition to the zinc finger protein include, e.g., effector domains from transcription factors (activators, repressors, co-activators, co-repressors), silencers, nuclear hormone receptors, oncogene transcription factors (e.g., myc, jun, fos, myb, max, mad, rel, ets, bcl, mos family members etc.); DNA repair enzymes and their associated factors and modifiers; DNA rearrangement enzymes and their associated factors and modifiers; chromatin associated proteins and their modifiers (e.g., kinases, acetylases and deacetylases); and DNA modifying enzymes (e.g., methyltransferases, topoisomerases, helicases, ligases, kinases, phosphatases, polymerases, endonucleases) and their associated factors and modifiers.

Transcription factor polypeptides from which one can obtain a regulatory domain include those that are involved in regulated and basal transcription. Such polypeptides include transcription factors, their effector domains, coactivators, silencers, nuclear hormone receptors (see, e.g., Goodrich et al., *Cell* 84:825-30 (1996) for a review of proteins and nucleic acid elements involved in transcription; transcription factors in general are reviewed in Bames & Adcock, *Clin. Exp. Allergy* 25 Suppl. 2:46-9 (1995) and Roeder, *Methods Enzymol.* 273:165-71 (1996)). Databases dedicated to transcription factors are known (see, e.g., *Science* 269:630 (1995)). Nuclear hormone receptor transcription factors are described in, for example, Rosen et al., *J. Med. Chem.* 38:4855-74 (1995). The C/EBP family of transcription factors are reviewed in Wedel et al., *Immunobiology* 193:171-85 (1995). Coactivators and co-repressors that mediate transcription regulation by nuclear hormone receptors are reviewed in, for example, Meier, *Eur. J. Endocrinol.* 134(2):158-9 (1996); Kaiser et al., *Trends Biochem. Sci.* 21:342-5 (1996); and Utley et al., *Nature* 394:498-502 (1998)). GATA transcription factors, which are involved in regulation of hematopoiesis, are described in, for example, Simon, *Nat. Genet.* 11:9-11 (1995); Weiss et al., *Exp. Hematol.* 23:99-107. TATA box binding protein (TBP) and its associated TAF polypeptides (which include TAF30, TAF55, TAF80, TAF110, TAF150, and TAF250) are described in Goodrich & Tjian, *Curr. Opin. Cell Biol.* 6:403-9 (1994) and Hurley, *Curr. Opin. Strict. Biol.* 6:69-75 (1996). The STAT family of transcription factors are reviewed in, for example, Barahmand-Pour et al., *Curr. Top.*

*Microbiol. Immunol.* 211:121-8 (1996). Transcription factors involved in disease are reviewed in Aso et al., *J. Clin. Invest.* 97:1561-9 (1996).

In one embodiment, the KRAB repression domain from the human KOX-1 protein is used as a transcriptional repressor (Thiesen et al., *New Biologist* 2:363-374 (1990); Margolin et al., *Proc. Nat'l Acad. Sci. USA* 91:4509-4513 (1994); Pengue et al., *Nucl. Acids Res.* 22:2908-2914 (1994); Witzgall et al., *Proc. Nat'l Acad. Sci. USA* 91:4514-4518 (1994)). In another embodiment, KAP-1, a KRAB co-repressor, is used with KRAB (Friedman et al., *Genes Dev.* 10:2067-2078 (1996)). Alternatively, KAP-1 can be used alone with a zinc finger protein. Other preferred transcription factors and transcription factor domains that act as transcriptional repressors include MAD (see, e.g., Sommer et al., *J. Biol. Chem.* 273: 6632-6642 (1998); Gupta et al., *Oncogene* 16:1149-1159 (1998); Queva et al., *Oncogene* 16:967-977 (1998); Larsson et al., *Oncogene* 15:737-748 (1997); Laherty et al., *Cell* 89:349-356 (1997); and Cultraro et al., *Mol Cell. Biol.* 17:2353-2359 (19977)); FKHR (forkhead in rhapdosarcoma gene; Ginsberg et al., *Cancer Res.* 15:3542-3546 (1998); Epstein et al., *Mol. Cell. Biol.* 18:4118-4130 (1998)); EGR-1 (early growth response gene product-1; Yan et al., *Proc. Nat'l Acad. Sci. USA* 95:8298-8303 (1998); and Liu et al., Cancer Gene Ther. 5:3-28 (1998)); the ets2 repressor factor repressor domain (ERD; Sgouras et al., *EMBO J.* 14:4781-4793 (1995)); and the MAD smSIN3 interaction domain (SID; Ayer et al., *Mol. Cell. Biol.* 16:5772-5781 (1996)).

In one embodiment, the HSV VP16 activation domain is used as a transcriptional activator (see, e.g., Hagmann et al., *J. Virol.* 71:5952-5962 (1997)). Other preferred transcription factors that could supply activation domains include the VP64 activation domain (Seipel et al., *EMBO J.* 11:4961-4968 (1996)); nuclear hormone receptors (see, e.g., Torchia et al., *Curr. Opin. Cell. Biol.* 10:373-383 (1998)); the p65 subunit of nuclear factor kappa B (Bitko & Barik, *J. Virol.* 72:5610-5618 (1998) and Doyle & Hunt, *Neuroreport* 8:2937-2942 (1997)); and EGR-1 (early growth response gene product-1; Yan et al., *Proc. Nat'l Acad. Sci. USA* 95:8298-8303 (1998); and Liu et al., *Cancer Gene Ther.* 5:3-28 (1998)).

Kinases, phosphatases, and other proteins that modify polypeptides involved in gene regulation are also useful as regulatory domains for zinc finger proteins. Such modifiers are often involved in switching on or off transcription mediated by, for example, hormones. Kinases involved in transcription regulation are reviewed in Davis, *Mol. Reprod. Dev.* 42:459-67 (1995), Jackson et al., *Adv. Second Messenger Phosphoprotein Res.* 28:279-86 (1993), and Boulikas, *Crit. Rev. Eukaryot. Gene Expr.* 5:1-77 (1995), while phosphatases are reviewed in, for example, Schonthal & Semin, *Cancer Biol.* 6:239-48 (1995). Nuclear tyrosine kinases are described in Wang, *Trends Biochem. Sci.* 19:373-6 (1994).

As described, useful domains can also be obtained from the gene products of oncogenes (e.g., myc, jun, fos, myb, max, mad, rel, ets, bcl, mos family members) and their associated factors and modifiers. Oncogenes are described in, for example, Cooper, *Oncogenes, The Jones and Bartlett Series in Biology* (2$^{nd}$ ed., 1995). The ets transcription factors are reviewed in Waslylk et al., *Eur. J Biochem.* 211:7-18 (1993) and Crepieux et al., *Crit. Rev. Oncog.* 5:615-38 (1994). Myc oncogenes are reviewed in, for example, Ryan et al., *Biochem. J.* 314:713-21 (1996). The jun and fos transcription factors are described in, for example, *The Fos and Jun Families of Transcription Factors* (Angel & Herrlich, eds. 1994). The max oncogene is reviewed in Hurlin et al., Cold Spring Harb. *Symp. Quant. Biol.* 59:109-16. The myb gene family is reviewed in Kanei-Ishii et al., *Curr. Top. Microbiol. Immunol.* 211:89-98 (1996). The mos family is reviewed in Yew et al., *Curr. Opin. Genet. Dev.* 3:19-25 (1993).

Zinc finger proteins can include regulatory domains obtained from DNA repair enzymes and their associated factors and modifiers. DNA repair systems are reviewed in, for example, Vos, *Curr. Opin. Cell Biol.* 4:385-95 (1992); Sancar, *Ann. Rev. Genet.* 29:69-105 (1995); Lehmann, *Genet. Eng.* 17:1-19 (1995); and Wood, *Ann. Rev. Biochem.* 65:135-67 (1996). DNA rearrangement enzymes and their associated factors and modifiers can also be used as regulatory domains (see, e.g., Gangloff et al., *Experientia* 50:261-9 (1994); Sadowski, *FASEB J.* 7:760-7 (1993)).

Similarly, regulatory domains can be derived from DNA modifying enzymes (e.g., DNA methyltransferases, topoisomerases, helicases, ligases, kinases, phosphatases, polymerases) and their associated factors and modifiers. Helicases are reviewed in Matson et al., *Bioessays*, 16:13-22 (1994), and methyltransferases are described in Cheng, *Curr. Opin. Struct. Biol.* 5:4-10 (1995). Chromatin associated proteins and their modifiers (e.g., kinases, acetylases and deacetylases), such as histone deacetylase (Wolffe, *Science* 272:371-2 (1996)) are also useful as domains for addition to the zinc finger protein of choice. In one preferred embodiment, the regulatory domain is a DNA methyl transferase that acts as a transcriptional repressor (see, e.g., Van den Wyngaert et al., *FEBS Lett.* 426:283-289 (1998); Flynn et al., *J. Mol. Biol.* 279:101-116 (1998); Okano et al., *Nucleic Acids Res.* 26:2536-2540 (1998); and Zardo & Caiafa, *J. Biol. Chem.* 273:16517-16520 (1998)). In another preferred embodiment, endonucleases such as Fok1 are used as transcriptional repressors, which act via gene cleavage (see, e.g., WO95/09233; and PCT/US94/01201).

Factors that control chromatin and DNA structure, movement and localization and their associated factors and modifiers; factors derived from microbes (e.g., prokaryotes, eukaryotes and virus) and factors that associate with or modify them can also be used to obtain chimeric proteins. In one embodiment, recombinases and integrases are used as regulatory domains. In one embodiment, histone acetyltransferase is used as a transcriptional activator (see, e.g., Jin & Scotto, *Mol. Cell. Biol.* 18:4377-4384 (1998); Wolffe, *Science* 272:371-372 (1996); Taunton et al., *Science* 272:408-411 (1996); and Hassig et al., *Proc. Nat'l Acad. Sci. USA* 95:3519-3524 (1998)). In another embodiment, histone deacetylase is used as a transcriptional repressor (see, e.g., Jin & Scotto, *Mol. Cell. Biol.* 18:4377-4384 (1998); Syntichaki & Thireos, *J. Biol. Chem.* 273:24414-24419 (1998); Sakaguchi et al., *Genes Dev.* 12:2831-2841 (1998); and Martinez et al., *J. Biol. Chem.* 273:23781-23785 (1998)).

Linker domains between polypeptide domains, e.g., between two zinc finger proteins or between a zinc finger protein and a regulatory domain, can be included. Such linkers are typically polypeptide sequences, such as poly gly sequences of between about 5 and 200 amino acids. Preferred linkers are typically flexible amino acid subsequences which are synthesized as part of a recombinant fusion protein. For example, in one embodiment, the linker DGGGS is used to link two zinc finger proteins. In another embodiment, the flexible linker linking two zinc finger proteins is an amino acid subsequence comprising the sequence TGEKP (see, e.g., Liu et al., *Proc. Nat'l Acad. Sci. USA* 5525-5530 (1997)). In another embodiment, the linker LRQKDGERP is used to link two zinc finger proteins. In another embodiment, the following linkers are used to link two zinc finger proteins: GGRR (Pomerantz et al. 1995, supra), (G4S)$_n$ (Kim et al., *Proc. Nat'l Acad. Sci. USA* 93, 1156-1160 (1996.); and GGRRGGGS; LRQRDGERP; LRQKDGGGSERP; LRQKD(G3S)$_2$ ERP.

Alternatively, flexible linkers can be rationally designed using computer program capable of modeling both DNA-binding sites and the peptides themselves (Desjarlais & Berg, *Proc. Nat'l Acad. Sci. USA* 90:2256-2260(1993), *Proc. Nat'l Acad. Sci. USA* 91:11099-11103 (1994) or by phage display methods.

In other embodiments, a chemical linker is used to connect synthetically or recombinantly produced domain sequences. Such flexible linkers are known to persons of skill in the art. For example, poly(ethylene glycol) linkers are available from Shearwater Polymers, Inc. Huntsville, Ala. These linkers optionally have amide linkages, sulfhydryl linkages, or heterofunctional linkages. In addition to covalent linkage of zinc finger proteins to regulatory domains, non-covalent methods can be used to produce molecules with zinc finger proteins associated with regulatory domains.

In addition to regulatory domains, often the zinc finger protein is expressed as a fusion protein such as maltose binding protein ("MBP"), glutathione S transferase ("GST"), hexahistidine, c-myc, and the FLAG epitope, for ease of purification, monitoring expression, or monitoring cellular and subcellular localization.

Expression Vectors and Introduction of Random Libraries into Cells

A. Cloning and expression of libraries encoding randomized zinc finger proteins

Nucleic acids encoding the randomized zinc finger proteins are typically cloned into vectors for transformation into prokaryotic or eukaryotic cells for replication, expression, and cell transformation. Such vectors are typically prokaryotic vectors, e.g., plasmids that act as shuttle vectors; eukaryotic vectors such as insect vectors, for storage, manipulation of the nucleic acid encoding zinc finger protein or production of protein; or eukaryotic vectors such as viral vectors (e.g., adenoviral vectors, retroviral vector, etc.) for expression of zinc finger proteins and regulation of gene expression. The nucleic acid encoding a zinc finger protein can then be administered to a plant cell, animal cell, a mammalian cell or a human cell, a fungal cell, a bacterial cell, or a protozoal cell.

To obtain expression of a cloned gene or nucleic acid, a zinc finger protein is typically subcloned into an expression vector that contains a promoter to direct transcription. Suitable bacterial and eukaryotic promoters are well known in the art and described, e.g., in Sambrook et al., *Molecular Cloning, A Laboratory Manual* (2nd ed. 1989); Kriegler, *Gene Transfer and Expression: A Laboratory Manual* (1990); and *Current Protocols in Molecular Biology* (Ausubel et al., eds., 1994). Bacterial expression systems for expressing the zinc finger protein are available in, e.g., *E. coli, Bacillus* sp., and *Salmonella* (Palva et al., *Gene* 22:229-235 (1983)). Kits for such expression systems are commercially available. Eukaryotic expression systems for mammalian cells, plant cells, yeast, and insect cells are well known in the art and are also commercially available.

The promoter used to direct expression of a zinc finger protein nucleic acid depends on the particular application. Either a constitutive or an inducible promoter is used, depending on the particular use of the clone encoding the zinc finger protein. Exemplary eukaryotic promoters include the CaMV 35 S plant promoter, SV40 early promoter, SV40 late promoter, metallothionein promoter, murine mammary tumor virus promoter, Rous sarcoma virus promoter, polyhedrin promoter, or other promoters shown effective for expression in eukaryotic cells.

The promoter typically can also include elements that are responsive to transactivation, e.g., hypoxia response elements, Gal4 response elements, lac repressor response element, and small molecule control systems such as tet-regulated systems and the RU-486 system (see, e.g., Gossen & Bujard, *Proc. Nat'l Acad. Sci. USA* 89:5547 (1992); Oligino et al., *Gene Ther.* 5:491-496 (1998); Wang et al., *Gene Ther.* 4:432-441 (1997); Neering et al., *Blood* 88:1147-1155 (1996); and Rendahl et al., *Nat. Biotechnol.* 16:757-761 (1998)).

In addition to the promoter, the expression vector typically contains a transcription unit or expression cassette that contains all the additional elements required for the expression of the nucleic acid in host cells, either prokaryotic or eukaryotic. For example, regulatory elements from eukaryotic viruses are often used in eukaryotic expression vectors, e.g., SV40 vectors, papilloma virus vectors, and vectors derived from Epstein-Barr virus.

A typical expression cassette thus contains a promoter operably linked, e.g., to the nucleic acid sequence encoding the zinc finger protein, and signals required, e.g., for efficient polyadenylation of the transcript, transcriptional termination, ribosome binding sites, or translation termination. Additional elements of the cassette may include, e.g., enhancers, and heterologous spliced intronic signals.

The particular expression vector used to transport the genetic information into the cell is selected with regard to the intended use of the zinc finger protein, e.g., expression in plants, animals, bacteria, fungus, protozoa, etc. (see, e.g., viral expression vectors described below and in the Example section). Standard bacterial expression vectors include plasmids such as pBR322 based plasmids, pSKF, pET23D, and commercially available fusion expression systems such as GST and LacZ. A preferred fusion protein is the maltose binding protein, "MBP." Such fusion proteins are used for purification of the zinc finger protein. Epitope tags can also be added to recombinant proteins to provide convenient methods of isolation, for monitoring expression, and for monitoring cellular and subcellular localization, e.g., c-myc or FLAG.

Some expression systems have markers for selection of stably transfected cell lines such as neomycin, thymidine kinase, hygromycin B phosphotransferase, and dihydrofolate reductase. High yield expression systems are also suitable, such as using a baculovirus vector in insect cells, with a zinc finger protein encoding sequence under the direction of the polyhedrin promoter or other strong baculovirus promoters.

The elements that are typically included in expression vectors also include a replicon that functions in *E. coli*, a gene encoding antibiotic resistance to permit selection of bacteria that harbor recombinant plasmids, and unique restriction sites in nonessential regions of the plasmid to allow insertion of recombinant sequences.

Standard transduction methods are used to produce bacterial, mammalian, yeast or insect cell lines that express the zinc finger proteins of the invention. Transformation of eukaryotic and prokaryotic cells are performed according to standard techniques (see, e.g., Morrison, *J. Bact.* 132:349-351 (1977); Clark-Curtiss & Curtiss, *Methods in Enzymology* 101:347-362 (Wu et al., eds. 1983). These methods include the lipofection, microinjection, ballistics, virosomes, liposomes, immunoliposomes, polycation or lipid:nucleic acid conjugates, naked DNA, artificial virions, agent-enhanced uptake of DNA, use of calcium phosphate transfection, polybrene, protoplast fusion, electroporation, plasmid vectors, viral vectors, both episomal and integrative, and any of the other well known methods for introducing cloned genomic DNA, cDNA, synthetic DNA or other foreign genetic material into a host cell (see, e.g., Sambrook et al., supra, see also U.S. Pat. Nos. 5,049,386, 4,946,787; 4,897,355; WO 91/17424, and WO 91/16024). It is only necessary that the particular genetic engineering procedure used be capable of successfully introducing at least one gene into the host cell capable of expressing the protein of choice.

B. Viral Vectors

A preferred method of delivering the libraries of the invention to cells is with viral vector delivery systems, including DNA and RNA viruses, which have either episomal or integrated genomes after delivery to the cell. The use of RNA or DNA viral based systems for the delivery of nucleic acids encoding randomized zinc finger protein take advantage of highly evolved processes for targeting a virus to specific cells in the body and trafficking the viral payload to the nucleus. Conventional viral based systems for the delivery of zinc finger proteins could include retroviral, lentiviral, adenoviral, adeno-associated, herpes simplex virus, and TMV-like viral vectors for gene transfer. Viral vectors are currently the most efficient and versatile method of gene transfer in target cells and tissues. Integration in the host genome is possible with the retrovirus, lentivirus, and adeno-associated virus gene transfer methods, often resulting in long term expression of the inserted transgene. Additionally, high transduction efficiencies have been observed in many different cell types and target tissues.

The tropism of a retrovirus can be altered by incorporating foreign envelope proteins, expanding the potential target population of target cells. Lentiviral vectors are retroviral vectors that are able to transduce or infect non-dividing cells and typically produce high viral titers. Selection of a retroviral gene transfer system would therefore depend on the target tissue. Retroviral vectors are comprised of cis-acting long terminal repeats with packaging capacity for up to 6-10 kb of foreign sequence. The minimum cis-acting LTRs are sufficient for replication and packaging of the vectors, which are then used to integrate the therapeutic gene into the target cell to provide permanent transgene expression. Widely used retroviral vectors include those based upon murine leukemiavirus (MuLV), gibbon ape leukemia virus (GaLV), simian immuno-deficiency virus (SIV), human immuno-deficiency virus (HIV), and combinations thereof (see, e.g., Buchscher et al., *J. Virol.* 66:2731-2739 (1992); Johann et al., *J. Virol.* 66:1635-1640 (1992); Sommerfelt et al., *Virol.* 176:58-59 (1990); Wilson et al., *J. Virol.* 63:2374-2378 (1989); Miller et al., *J. Virol.* 65:2220-2224 (1991); PCT/US94/05700).

In applications where transient expression of the zinc finger protein is preferred, adenoviral based systems are typically used. Adenoviral based vectors are capable of very high transduction efficiency in many cell types and do not require cell division. With such vectors, high titer and levels of expression have been obtained. This vector can be produced in large quantities in a relatively simple system. Adeno-associated virus ("AAV") vectors are also used to transduce cells with target nucleic acids (see, e.g., West et al., *Virology* 160: 38-47 (1987); U.S. Pat. No. 4,797,368; WO 93/24641; Kotin, *Human Gene Therapy* 5:793-801 (1994); Muzyczka, *J. Clin. Invest.* 94:1351 (1994). Construction of recombinant AAV vectors are described in a number of publications, including U.S. Pat. No. 5,173,414; Tratschin et al., *Mol. Cell. Biol.* 5:3251-3260 (1985); Tratschin et al., *Mol. Cell. Biol.* 4:2072-2081 (1984); Hermonat & Muzyczka, *Proc. Nat'l Acad. Sci. USA* 81:6466-6470 (1984); and Samulski et al., *J. Virol.* 63:03822-3828 (1989).

Packaging cells are used to form virus particles that are capable of infecting a host cell. Such cells include 293 cells, which package adenovirus, and ψ2 cells or PA317 cells, which package retrovirus. Viral vectors used in gene therapy are usually generated by producer cell line that packages a nucleic acid vector into a viral particle. The vectors typically contain the minimal viral sequences required for packaging and subsequent integration into a host, other viral sequences being replaced by an expression cassette for the protein to be expressed. The missing viral functions are supplied in trans by the packaging cell line. For example, AAV vectors typically only possess ITR sequences from the AAV genome which are required for packaging and integration into the host genome. Viral DNA is packaged in a cell line, which contains a helper plasmid encoding the other AAV genes, namely rep and cap, but lacking ITR sequences. The cell line is also infected with adenovirus as a helper. The helper virus promotes replication of the AAV vector and expression of AAV genes from the helper plasmid. The helper plasmid is not packaged in significant amounts due to a lack of ITR sequences. Contamination with adenovirus can be reduced by, e.g., heat treatment to which adenovirus is more sensitive than AAV.

In many situations, it is desirable that the vector be delivered with a high degree of specificity to a particular cell type. A viral vector is typically modified to have specificity for a given cell type by expressing a ligand as a fusion protein with a viral coat protein on the viruses outer surface. The ligand is chosen to have affinity for a receptor known to be present on the cell type of interest. For example, Han et al., *Proc. Nat'l Acad. Sci. USA* 92:9747-9751 (1995), reported that Moloney murine leukemia virus can be modified to express human heregulin fused to gp70, and the recombinant virus infects certain human breast cancer cells expressing human epidermal growth factor receptor. This principle can be extended to other pairs of virus expressing a ligand fusion protein and target cell expressing a receptor. For example, filamentous phage can be engineered to display antibody fragments (e.g., FAB or Fv) having specific binding affinity for virtually any chosen cellular receptor. Although the above description applies primarily to viral vectors, the same principles can be applied to nonviral vectors. Such vectors can be engineered to contain specific uptake sequences thought to favor uptake by specific target cells.

Assays for Determining Regulation of Gene Expression by Zinc Finger Proteins A variety of assays can be used to screen for phenotypic changes upon transduction of cells with the library encoding randomized zinc finger proteins. A phenotype can be assessed by measuring, e.g., protein or mRNA levels, product levels, enzyme activity; transcriptional activation or repression of a reporter gene; second messenger levels (e.g., cGMP, cAMP, IP3, DAG, $Ca^{2+}$); cytokine and hormone production levels using, e.g., immunoassays (e.g., ELISA and immunohistochemical assays with antibodies), hybridization assays (e.g., RNase protection, northerns, in situ hybridization, oligonucleotide array studies), calorimetric assays, amplification assays, enzyme activity assays, and other phenotypic assays.

For high throughput applications, typically either cells are pooled and transduced in a batch, and then individually screened using flow cytometry, or the cells are pooled into clonal arrays and screened, e.g., with liquid robotics (see Example section). Examples of assays for a selected phenotype include e.g., changes in proliferation, anchorage dependence, growth factor dependence, foci formation, and growth in soft agar; apoptosis assays, e.g., DNA laddering and cell death, expression of genes involved in apoptosis; signal transduction assays, e.g., changes in intracellular calcium, cAMP, cGMP, IP3, changes in hormone and neurotransmittpr release; receptor assays, e.g., estrogen receptor and cell growth; growth factor assays, e.g., EPO, hypoxia and erythrocyte colony forming units assays; enzyme production assays, e.g., FAD-2 induced oil desaturation; pathogen resistance assays, e.g., insect, bacterial, and viral resistance assays; chemical production assays, e.g., penicillin production; transcription assays, e.g., reporter gene assays; and protein production assays, e.g., VEGF ELISAs.

In one embodiment, the assay for the selected phenotype is performed in vitro. In one preferred assay format, zinc finger protein regulation of gene expression in cultured cells is examined by determining protein production using an ELISA assay or an immunoassay such as fluorescence activated cell sorting.

In another embodiment, zinc finger protein regulation of gene expression is determined by measuring the level of target gene mRNA expression. The level of gene expression is measured using amplification, e.g., using PCR, LCR, or hybridization assays, e.g., northern hybridization, RNase protection, dot blotting. RNase protection is used in one embodiment. The level of protein or mRNA is detected using directly or indirectly labeled detection agents, e.g., fluorescently or radioactively labeled nucleic acids, radioactively or enzymatically labeled antibodies, and the like, as described herein.

Alternatively, a reporter gene system, e.g., that measures activation of a gene in a pathway, can be devised using a promoter operably linked to a reporter gene such as luciferase, green fluorescent protein, CAT, or β-gal. The reporter construct is typically co-transfected into a cultured cell. After treatment with the zinc finger protein of choice, the amount of reporter gene transcription, translation, or activity is measured according to standard techniques known to those of skill in the art.

Identification and Isolation of Genes Associated with a Selected Phenotype

After assaying for phenotypic changes, as described above, those cells exhibiting an altered phenotype are selected for further study, in which the genes associated with the change in phenotype are identified and isolated. The genes are identified and isolated, e.g., using differential gene expression analysis with microarrays; reverse genetics; e.g., identification of genes using zinc finger proteins to probe YAC or BAC clones and using zinc finger proteins to scan genomic sequences; subtractive hybridization; differential cDNA cloning frequencies, subtractive hybridization; by cloning ESTs from cells of interest; by identifying genes that are lethal upon knockout; by identifying genes that are up- or down-regulated in response to a particular developmental or cellular event or stimuli; by identifying genes that are up- or down-regulated in certain disease and pathogenic states; by identifying mutations and RFLPs; by identifying genes associated with regions of chromosomes known to be involved in inherited diseases; by identifying genes that are temporally regulated, e.g., in a pathogenic organism; differences based on SNPs; by cross-linking the zinc finger protein to the DNA with which it is associated, followed by immunoprecipitation of the zinc finger protein and sequencing of the DNA, etc.

In one embodiment, the candidate genes are identified by comparing patterns of gene expression associated with the phenotypic change. For instance, down regulation of a gene by a ZFP-KRAB will result in under representation of the corresponding mRNA when compared to a control (i.e., KRAB alone). There are several methods that can be employed to compare patterns of gene expression including differential hybridization screening (see, e.g., Tedder et al., *Proc. Nat'l Acad. Sci. USA* 85:208-212 (1988)), subtractive library construction (see, e.g., Davis et al., *Nature* 308:149-153 (1984)), representational difference analysis (RDA) (see, e.g., Hubank, *Nucleic Acid Res* 22:5640-5648 (1994)); Lisitsyn et al., *Science* 259:640-648 (1993)) differential display (see, e.g., Liang et al., *Nucleic Acid Res* 21:3269-3275 (1993); Liang et al., *Science* 257:967-971 (1992)), conventional cDNA array hybridization (see, e.g., Schummer et al., *Biotechniques* 23:1087-1092 (1997)) and serial analysis of gene expression (SAGE) (see, e.g., Velculescu et al., *Science* 276:1268-1272 (1997)).

In another embodiment, a technique called suppression subtractive hybridization (SSH) is used, which is a modification of the RDA as it normalizes for mRNA abundance (see, e.g, Daitchenko et al., *Proc. Natl. Acad. Sci. USA* 93:6025-6030 (1996)). This technique will be used to compare gene expression profiles of a target cell pre-and-post zinc finger protein transfection. This SSH cDNA library may be further screened using microarrays containing oligonucleotide libraries representing cDNA from relevant tissue types or, ultimately, oligonucleotides representing all open reading frames in the entire genome. This combined screening of SSH cDNA libraries and microchip arrays screening will allow for the identification of putative functions and pathway relationships for uncharacterized genes.

Bacterial artificial chromosomes (BAC) or yeast artificial chromosomes (YAC) containing large chromosomal segments representing the entire human genome can be employed to determine the gene (or genes) responsible for the observed phenotype. YAC or BAC clones containing the candidate gene can be identified by physical capture using zinc finger protein or, alternatively, by probing arrayed clones.

Direct capture relies on physically binding and separating clones containing target DNA from the overall population of clones. Candidate zinc finger proteins are added to BAC or YAC libraries, using buffer conditions equivalent to those used in biochemical analysis of zinc finger proteins (see, e.g., co-owned U.S. Pat. Nos. 6,534,261 and 6,453,242). Certain factors should be carefully adjusted so as to optimize specific binding by the zinc finger protein. Important chemical factors are zinc and salt (usually either potassium or sodium chloride). Zinc ion concentration should be 10 micromolar or less and salt should be 50 millimolar or more. zinc finger protein and library DNA is added to the buffer. The amounts of each reactant is important. Highest specificity is obtained when the zinc finger protein is added at a concentration that is below the dissociation constant (as judged by gel shifts) of the protein for its designed target. The reaction is allowed to equilibrate at room temperature.

Modifications could include performing the initial binding at protein concentrations above the dissociation constant in order to maximize binding. The process could be repeated using only the retained clones with concentrations of proteins that maximize specificity (i.e., slightly below the dissociation constant). Another variation is separating clones into pools rather than employing the entire library. The number of discrete clones in each pool would depend on the total library size. For a library size of 1,000,000 clones, ten pools of 100,000 clones or 100 pools of 10,000 clones and so on could be employed. Following equilibration, the ZFP:DNA complex can be removed from the bulk solution by affinity capture of the zinc finger protein. Potential ligands are FLAG, MBP, biotin, 6xHis or any other tag for which an acceptable receptor exists. The receptor should be immobilized to an inert support such as magnetic beads or sepharose resin. Appropriate receptors would be FLAG antibody (FLAG epitope), amylose (MBP), streptavidin (biotin), nickel (6xHis).

Once the clones are identified by capture they are sequenced to identify coding regions. The genomic inserts cloned into the BACs or YACs may be too large to pinpoint the exact gene responsible for the phenotype. The list of possible candidate genes within a clone could be narrowed in the cases where clones with overlapping, but not identical, sequences were captured. Only the regions common to both clones should contain the candidate genes. Alternatively, clones containing smaller segments of each BAC and YAC could then be used for capture. Other vectors used could include lamba, P1 or cosmids.

In another embodiment, physical capture and retention of DNA in solution is an array-based method where zinc finger proteins are used as probes to detect clones possessing the correct target sequences. BAC and YAC libraries would be arrayed so that each clone would occupy an unique address on a support such as glass, nitrocellulose or any other material which allows nondestructive immobilization of DNA. The zinc finger proteins would be conjugated to a fluorophore either pre- or posttranslationally. The supports containing the clones would be flooded with the zinc finger protein and incubated for a sufficient time to allow binding. Then unbound zinc finger protein would be washed off using conditions that minimize non-specific binding. Binding would be visualized by exposing the filter to an appropriate wavelength of light, exciting the fluorophore to emit at a characteristic wavelength.

This method could be refined by simultaneously adding two zinc finger proteins labeled with different fluorophores. By using the fluorophores emitting at appropriate wavelengths, binding of both zinc finger proteins to the same clone could be detected simultaneously by monitoring the output color which should be a combination of both wavelengths. For instance, the presence of a blue emitting fluorophore and a yellow emitting fluorophore would produce green light. Flurophores could be fluorescent proteins that are modified from green fluorescent protein to produce the spectrum of wavelengths. Alternatives would be fluorescent dyes with reactive groups that can be conjugated to protein moieties post purification or fluorescently labeled antibodies. As with physical capture, once a BAC or YAC clone is identified different regions can be probed in sublibraries with shorter inserts.

In another embodiment, physical capture is achieved by tagging DNA targets which are bound by their specific zinc finger protein by using a modified catalyzed reporter deposition (CARD) method. CARD has been used as a means of signal amplification in immunocytochemistry, ELISA, and blotting (Adams, *J. Histochem. Cytochem.* 40:1457-1463 (1992); Bobrow et al., *J. Immunol. Meth.* 150:145-149 (1992)). This technique nonally involves the use of horseradish peroxidase (HRP) in the presence of hydrogen peroxide to catalyze biotinylated tyramine deposition around the site of the enzyme activity. This results in biotinylation of molecules or motifs that are proximal to the active enzyme. This technique has been adapted to allow the specific recovery of neighboring phage antibodies binding around a core ligand binding site on a cell surface (Osbourn et al., *Nat. Biotech.* 16:778-781 (1998)).

A modified CARD technique would be used to biotinylate genes which have been recognized by the randomized zinc finger proteins of the invention. The zinc finger proteins could be either directly engineered as HRP fusions, or HRP conjugated antibodies which recognize the zinc finger proteins (by their FLAG sequence for instance) could be used. HRP conjugated anti-FLAG monoclonal antibody and biotin tyramine are added to an equilibrated solution of zinc finger proteins and libraries. In either scenario, the biotin which is covalently attached to DNA sequences surrounding the zinc finger proteins, and this biotin "tag" will provide a handle for further manipulation. The biotinylated DNAs can be captured and purified with streptavidin-coated magnetic beads (Dynal, Oslo). Another way to capture the DNAs that are recognized by zinc finger proteins is to use an anti-FLAG affinity column to purify the DNAs. Post capture the DNAs will be cloned, sequenced and otherwise characterized.

In another embodiment, genes are identified by scanning genomic sequences. The target gene sequence can be predicted based on the recognition residues of each zinc finger. By using these rules for amino acid side-chain contacts with nucleotide bases, the nucleotide sequence can be "read off" of the zinc finger protein. Allowances for ambiguities can be made based on a knowledge of specificity for each interaction or combinations of interactions. Genes can be identified by searching the Genbank DNA database (National Center of Biotechnology Information) for matching sequences using an algorithm such as BLAST (Altschul et al., *J. Mol. Biol.* 215: 403-410 (1990)). Ultimately it will be possible to search the whole human genome. The expectation is that many of the zinc finger proteins targeting candidate genes will recognize different sequences of the same gene or genes. Thus, confirmation that any one zinc finger protein is truly targeting a particular gene is obtained by grouping the genes identified by different zinc finger proteins and deriving a consensus.

In another embodiment, genes are identified by cross linking the zinc finger protein and the nucleic acid (or chromatin) to which it is bound, immunoprecipitating the cross-linked complex, and then sequencing the nucleic acid to identify the gene of interest. Sequence-specific binding of a zinc finger protein to chromatin is assayed, e.g., by chromatin immunoprecipitation (ChIP). Briefly, this technique involves the use of a specific antibody to immunoprecipitate chromatin complexes comprising the corresponding zinc finger protein antigen, and examination of the nucleotide sequences present in the immunoprecipitate. Immunoprecipitation of a particular sequence by the antibody is indicative of interaction of the zinc finger protein antigen with that sequence (see, e.g., O'Neill et al. in *Methods in Enzymology, Vol.* 274, pp. 189-197 (1999); Kuo et al., *Method* 19:425-433 (1999); and Ausubel et al., *Current Protocols in Molecular Biology,* Chapter 21 (1987 and periodic updates).

In one embodiment, the chromatin immunoprecipitation technique is applied as follows. The zinc finger protein is introduced into a cell and, after a period of time sufficient for binding of the zinc finger protein to its binding site has elapsed, cells are treated with an agent that crosslinks the zinc finger protein to chromatin if that molecule is stably bound. The zinc finger protein can be crosslinked to chromatin by, for example, formaldehyde treatment or ultraviolet irradiation. Subsequent to crosslinking, cellular nucleic acid is isolated, sheared and incubated in the presence of an antibody directed against the zinc finger protein. Antibody-antigen complexes are precipitated, crosslinks are reversed (for example, formaldehyde-induced DNA-protein crosslinks can be reversed by heating) and the sequence content of the immunoprecipitated DNA is tested for the presence of a specific sequence, for example, the target site of the zinc finger protein.

In a preferred embodiment, the immunoprecipitated DNA is tested for the presence of specific sequences by a sensitive hydrolyzable probe assay allowing real-time detection of an amplification product, known colloquially as the Taqman® assay. See U.S. Pat. No. 5,210,015; Livak et al., PCR *Meth. App.* 4:357-362 (1995); and Heid et al., *Genome Res.* 6:986-994 (1995). Briefly, an amplification reaction (e.g., PCR) is conducted using a probe designed to hybridize to a target sequence flanked by two amplification primers. The probe is labeled with a fluorophore and a fluorescence quencher such that, when not hybridized to its target sequence, the probe does not emit detectable fluorescence. Upon hybridization of the probe to its target and hydrolysis of the probe by the polymerase used for amplification, the fluorophore is released from the vicinity of the quencher, and fluorescence increases in proportion to the concentration of amplification product. In this assay, the presence of increased levels of an amplification product corresponding to the binding site for the zinc finger protein, compared to levels of amplification product specific to a control genomic sequence, in indicative of binding of the zinc finger protein to its binding site in cellular chromatin (see also co-owned WO 01/83751, the disclosure of which is herein incorporated by reference in its entirety).

Additional methods for detecting binding of zinc finger protein to chromatin include, but are not limited to, microscopy (e.g., scanning probe microscopy), fluorescence in situ hybridization (FISH) and fusion of a DNA methylase domain to the zinc finger protein, in which case sequences to which the zinc finger protein is bound become methylated and can be identified, for example, by comparing their sensitivity to methylation-sensitive and methylation-dependent restriction enzymes or by using antibodies to methylated DNA (see, e.g., van Steensel et al., *Nature Biotechnology* 18:424-428 (2000)).

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to one of ordinary skill in the art in light of the teachings of this invention that certain changes and modifications may be made thereto without departing from the spirit or scope of the appended claims.

EXAMPLES

The following examples are provided by way of illustration only and not by way of limitation. Those of skill in the art will readily recognize a variety of noncritical parameters that could be changed or modified to yield essentially similar results.

Example 1

Protocol for Preparation and Screening Using a Randomized Zinc Finger Protein Library Generated by Finger Grating A. Generation of a library using finger grafting A library of 12 different helices compatible with 5 different finger positions will be created and assembled into zinc finger proteins using a method similar to that currently used to assemble engineered 3 finger proteins (see, e.g., U.S. Ser. No. 09/229,037 filed Jan. 12, 1999, and U.S. Ser. No. 09/229,007, filed Jan. 12, 1999). Randomness will be confirmed by sequencing a representative sample. Of this library, 250,000 individual bacterial transformants will be picked and archived. The individual transformants will be combined into pools of 8 and cloned into a viral delivery vector (such as an adenoviral vector).

Viral delivery particles will be produced from each pool (there are 31,250 different pools) and tested in an appropriate assay for the identification of a desired phenotype. Assays could be the development of growth factor independence, secretion of EPO, angiogenesis, apoptosis etc.

Biologically active zinc finger proteins ("hits") will be confirmed by secondary screening. The gene directly responsible for the phenotype will be identified either by virtue of proximity of a binding site (the binding site for the active zinc finger protein can be surmised by helix composition or determined experimentally by site selection) if the sequence is known, or pulled from a genomic library using the zinc finger protein itself as a molecular probe.

Specific recognition helices for twelve different DNA triplet sequences have been characterized. These helices are referred to by their "SBS" numbers. The table below shows the target DNA triplet sequences and the amino acid composition of the twelve different recognition helices. Any 5-finger zinc finger protein comprising a unique subset of 5 of these 12 recognition helices will recognize a distinct and unique 15 basepair DNA sequence.

TABLE 1

| SBS Number | Target Triplet | Recognition Helix |
| --- | --- | --- |
| SBS1 | GTG | RSDALTR |
| SBS2 | GAG | RSDNLAR |
| SBS3 | GGG | RSDHLSR |
| SBS4 | GCG | RSDELTR |
| SBS5 | GCA | QSGSLTR |
| SBS6 | GCT | QSSDLTR |
| SBS7 | GCC | ERGTLAR |
| SBS8 | GAT | QSSNLAR |
| SBS9 | GAC | DRSNLTR |
| SBS10 | GAA | QSGNLAR |
| SBS11 | GGC | DRSHLAR |
| SBS12 | GGA | QSGHLQR |

For example, a zinc finger protein made up of (reading from the C-terminus) SBS 4-10-9-10-2 would recognize the DNA sequence (reading 5' to 3') GCG GAA GAC GAA GAG.

DNA encoding each of the 12 SBS helices are synthesized as oligonucleotides. These oligonucleotides are mixed in equimolar amounts and combined with oligonucleotides that encode the remaining amino acids of a five finger zinc finger protein based on the amino acid sequence of the murine zinc finger protein Zif268. This mixture is PCR amplified as described in U.S. Ser. No. 09/229,037, filed Jan. 12, 1999, and U.S. Ser. No. 09/229,007, filed Jan. 12, 1999, and subcloned into two different mammalian expression such that one vector produces a chimeric transcription factor comprising a nuclear localization sequence, the zinc finger protein DNA binding domain, the VP16 activating domain and the FLAG epitope tag (this vector is referred to using an acronym of its component parts; NVF). The second vector is identical to the first except that a KRAB transcriptional repression domain replaces the VP16 domain (NKF). The rest of the vector sequences support the production of virus-based delivery components such as the sequences required for recombination into adenoviral vectors and packaging into viral particles These vectors are used to transform *E. coli*. Individual colonies, representing distinct individual zinc finger protein clones, are picked and subcultured in 96-well microtiter dishes. 250,000 clones are picked and arrayed for each vector system (NVF and NKF). This creates an arrayed zinc finger protein library comprising approximately 2,600 microtiter plates. These libraries are stored as glycerol stocks at −80° C.

DNA sequence analysis of a subset of each library confirms that the five finger zinc finger proteins encoded represent a random assortment of the 12 recognition helices.

The zinc finger protein *E. coli* clone library is converted to a pooled viral delivery library as follows. The *E. coli* clones are arranged into pools of 8 different clones by pipetting adjacent wells together using a 12-channel multi-channel pipette (this can be done robotically). The pools are grown in rich medium using deep-well microtiter dishes at 37° C. Plasmid DNA is prepared using Qiagen columns. The DNA pools are then used to transfect PERC.6 cells (a cell line used to produce adenoviral vectors). Several days later the viral vector-laden culture supernatants are collected and stored at −80° C.

B. Screening for the selected phenotype

An assay for a particular desired phenotype is now created and implemented using a microtiter-based method. The viability of a growth factor dependent cell line, capable of detecting autocrine production of a growth factor such as EPO or VEGF is one such assay, described below.

Once the assay is created, the influence of the zinc finger protein library members on the assay can be determined using robotic methods commonly employed in the high throughput screening industry. A sample, in this case a pool of 8 different zinc finger proteins carried in adenoviral delivery vectors, is added to a well of an assay plate, in this case a growth factor dependent cell line in minimal medium. Several days later the assay plate is tested to determine if any of the zinc finger proteins caused the cell line to grow. Growth can be determined using many different high throughput assays, in this case by the metabolic conversion of a fluorescent dye Alamar Blue.

Hits from the high throughput assay (wells where cell growth was supported) are confirmed by simply retesting the pool and then the pool is "deconvoluted," separating it into individual zinc finger protein component members and retested to determine which of the 8 zinc finger proteins triggered cell growth.

Once a zinc finger protein-phenotype connection has been established, mechanistic and genomic analyses can be performed to identify the gene responsible for the phenotype. In this case, the independence of growth factors suggests autocrine production of a growth factor. This can be simply confirmed by testing the growth supporting nature of zinc finger protein treated conditioned medium on otherwise untreated growth factor dependent cells.

After the autocrine mechanism has been confirmed, the task becomes one of determining which growth factor gene was switched on by the zinc finger protein library member. Well characterized growth factors can be eliminated by using inactivating antibodies. Suspect genes can be identified by scanning the sequence databases for the 15 basepairs recognized by the active zinc finger protein. This sequence can be determined either by simply reading off the recognition helices' amino acid sequence and predicting the DNA target sequence using the relationships outlined in the table above, or by using site selection experiments as described in previous applications to determine the DNA target sequence empirically. Suspect (or candidate) genes can also be identified using experimental method designed to measure global differential gene expression (such as gene expression microarrays). Finally, the zinc finger protein itself can be used as a probe for YAC or BAC clones to identify candidate loci.

C. Screening using flow cytometry

In addition to screening using microtiter type assays (as described above), flow cytometry and cell sorting can be used to screen for specific phenotypes. A flow cytometer simply measures the fluorescence of one cell at a time as a stream of cells flow past a laser. Multiple lasers and multiple detectors permit simultaneous detection of several fluorophores (typically up to 4). A wide variety of fluorescent probes have been developed allowing the measurement of cell surface markers, DNA content, green fluorescent protein and other cytoplasmic components. Multi-marker analysis allows one to study a specific cell population, defined by specific cell surface markers, in complex mixtures of cells such as whole blood. In addition to simply detecting the kind and intensity of specific fluorescent markers on cells as they flow past the laser beams, cytometers with sorting capability can collect specific populations of cells one cell at a time. This permits the outgrowth of very specific cell populations (if the labeling method is not toxic, not always the case) and/or the application of bulk-type assays (western blots, northern blots etc.) on homogeneous and very specific populations of cells.

In screening, a cell softer permits the isolation of a single cell or a population of cells displaying a desired phenotype. This could be the appearance of a specific receptor on the surface of a cell treated by a specific cytokine (i.e. the appearance of ICAM on the surface of cells treated with IL-1) or any other measurable response.

In practice, a library is created in retroviral vectors. This could be the same zinc finger protein library described above. Susceptible cells (for example U937 monocytic cells) are transduced using the retroviruses. A specific phenotype is detected using flow cytometry and cells displaying the desired phenotype collected into separate wells of a microtiter plate. The zinc finger proteins causing the desired phenotype can then identified by rescuing the retroviral sequences using PCR.

Example 2

Protocol for Preparation and Screening Using a Randomized Zinc Finger Protein Library Generated by Codon Doping A. Preparation of the library using codon doping As described above, each zinc finger binds three nucleotides using four critical amino acids in the recognition helix. If each base in the codons for these amino acids was simply randomized, it would generate a library of $4^{12}$ clones (1.7 million). This number is already in excess of a desired library limit of about one million to about 10 or 100 million clones and only concerns one finger (and three are to be used in these methods). However, it is not necessary to use completely random codons. Because of the redundancy of the genetic code, schemes of semi-randomization can generate representatives of all, or nearly all codons. This strategy is thus called a codon doping scheme.

One randomization scheme uses VNS instead of NNN, where N=any base, V=A or G and S=G or C. All of the codons are represented by VNS except Phe, Trp, Tyr, Cys and all translation termination codons. It is advantageous to eliminate the termination codons and loss of the four amino acids listed is tolerable because they are typically underrepresented in known protein DNA contacts. With the VNS scheme it is possible to randomize 4 amino acids in significantly less than a million clones (331,776 to be exact). However, varying a fifth position pushes the library size into the 8 million clone range. Some finger positions will still need to be fixed. The four critical amino acids of finger 1 will be randomized using the VNS scheme and fingers 2 and 3 will be fixed to recognize the DNA sequence GGG GAG. Specific fingers for these triplets are available that do not recognize alternative binding sites. This 6 base pair anchoring sequence will occur once every $4^6$ (4096) bases and should lie within a reasonable distance of the transcription initiation site of most genes. The randomized finger will direct the zinc finger proteins to subsets of these anchoring sites with 3 or 4 additional bases of sequence specificity. In future experiments additional libraries can be examined that carry alternative anchoring fingers.

The mutagenesis strategies proposed to generate the three-finger zinc finger protein library is represented below:

TABLE 2

|  | −1 | 1 | 2 | 3 | 4 | 5 | 6 |
|---|---|---|---|---|---|---|---|
| Finger 1 | VNS | S | VNS | VNS | L | A | VNS |
| Finger 2 | R | S | D | N | L | A | R |
| Finger 3 | R | S | D | H | L | S | R |

To balance the diversity and size of the zinc finger protein library, the relatively highly conserved serine is fixed at position 1; leucine at position 4 (which does not contact DNA but is involved in stabilizing the fold of the finger); and a small alanine at position 5. All the randomization will be built in by polymerase chain reaction using 3 degenerate oligos (2, 4, and 6) that contain the VNS dope schemes for the −1, 2, 3, and 6 positions (FIG. 1).

Codon doping protocol
1. Dilute the following oligos to 0.5 µM in $H_2O$
Oligo 1: SCOM (Sangamo Common Oligo) 1
Oligo 2: Oligo encoding randomized finger 1:

(VNS)S(VNS)(VNS)LA(VNS), see text for explanation of notation.
Oligo 3: SCOM 2
Oligo 4: Oligo encoding finger 2: RSDNLAR
Oligo 5: SCOM 3
Oligo 6: Oligo encoding finger 3: RSDHLSR
2. Set up PCR reactions as follows:
50 µl 2×PCR Master Mix, Boehringer Mannheim
1 µl SCOM 1
1 µl SCOM 2
1 µl SCOM 3
1 µl Randomized Finger 1 oligo
1 µl Finger 2 oligo
1 µl Finger 3 oligo
44 µl $H_2O$
100 µl total volume
3. Run the following PCR program to form the initial "scaffold" of oligos (see diagram):
95° C. 5 minutes; 95° C. 30 seconds; 40° C. 30 seconds×4 cycles 72° C. 1 minute
4. Then add external primers (SCOM F, at 10 µM, and SCOM R, at 10 µM), 2 µl of each primer (refer to diagram).
5. Continue with the following PCR program:
95° C. 1 minute; 95° C. 30 second; 62° C. 30 seconds×30 cycles
72° C. 1 minute
72° C. 10 minutes
4° C. soak
6. Run entire reaction through Qiagen PCR Clean-up column. Elute in 50 µl $H_2O$
7. Set up Kpn I/Bam HI restriction digest:
50 µl clean PCR product
10 µl NEB Bam HI Buffer, 10×
10 µl NEB BSA, 10×
3 µl NEB Kpn I restriction enzyme, u/l
2 µl NEB Bam HI restriction enzyme, u/l
25 µl $H_2O$
100 µl total volume, incubate at 37° C. for 4 hours.
8. Run entire digest on a 1.4% agarose gel (split sample into two lanes). Gel extract and purify the 300 bp fragment from each lane using Qiagen Gel Extraction Kit. Elute each in 30 µl $H_2O$, then combine for total volume of 60 µl.
9. Ligate into a phage vector such as SurfZAP (Stratagene) hat has been modified to possess Kpn I and Bam HI restriction sites in the appropriate frame as to generate a plasmid encoding ZFP-cpIII fusion protein.
10. Transform into XL-1 Blue bacteria and plate onto LB+ 100 g/ml ampicillin. Grow overnight at 37° C.
11. Pick individual colonies and sequence to ensure that finger 1 randomization is sufficiently represented.

B. Packaging into viral vectors for delivery
This step entails cloning the zinc finger protein libraries from the donor phage vectors into an AAV (adeno-associated viral) vector. Each vector will retain an intact cis-acting ITR sequence, followed by a cytomegalovirus promoter. The ITR sequences are required in cis to provide functional origins of replication (ori) as well as the signals for encapsidation, integration into the cell genome and rescue from either host cell chromosomes or recombinant plasmids. To maintain an optimal wild-type AAV genome size for the vectors, an additional, functionally inert intron sequence will be incorporated into the DNA construct. This intron will be spliced out in the final mRNA that would encode the functional zinc finger protein. The zinc-finger genes will be modified to incorporate a Kozak sequence for proper translation initiation and add a nuclear localization sequence such as that from the SV40 T antigen. The sequence for the assembled zinc finger protein expression constructs will be as follows: Kozak sequence-NLS-ZFPs-KRAB/VP16-FLAG.

Figure 3:
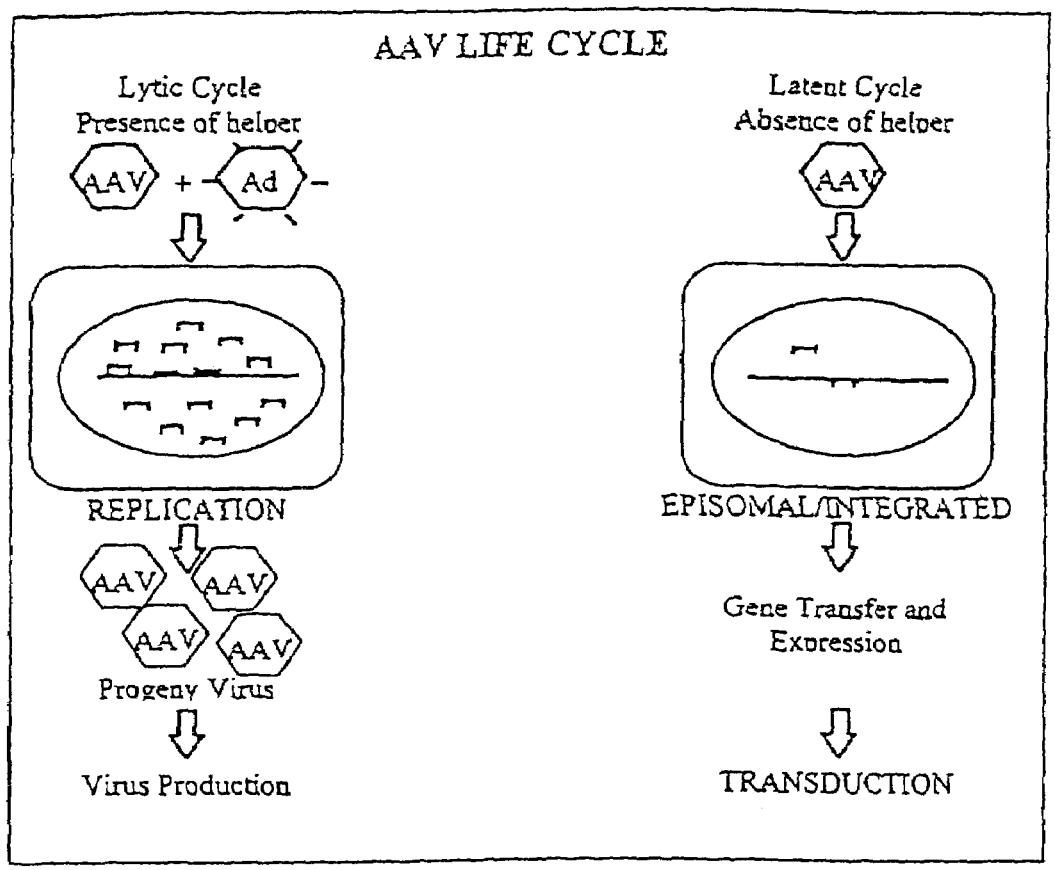
FIG. 3 shows the life cycle of an adeno-associated virus.

Two distinguishable phases of the AAV life cycle can occur in permissive or non-permissive conditions (see FIG. 3). In permissive cells, the presence of a helper virus, typically adenovirus, causes an infecting AAV genome to be greatly amplified generating a large burst of infectious progeny. This biological property will be exploited to generate AAV-ZFP vectors at genomic scale as well as to rescue inserts from relevant target cells if needed.

In a productive infection, the infecting parental AAV single strand genome is converted to a parental duplex replicating form (RF) by a self-priming mechanism which takes advantage of the ability of the ITR to form a hairpin structure. This process can occur in the absence of helper virus but is enhanced by a helper virus. The parental RF molecule is then amplified to form a large pool of progeny RF molecules in a process which requires both the helper functions and the AAV rep gene products, Rep78 and Rep68. AAV RF genomes are precursors to progeny single strand (SS) DNA genomes that are packaged into pre-formed empty AAV capsids composed of VP1, VP2 and VP3 proteins.

In the absence of a helper virus the AAV genomes reach the cell nucleus but bulk replication generally does not occur. The infecting genomes are converted to double stranded DNA (dsDNA) and may persist as free unintegrated genomes for a considerable number of cell passages. Expression of exogenous vector genes can occur from these dsDNA forms and these vector sequences can be rescued through packaging into new viral particles. These new viral particles are generated by induction of cell permissiveness through infection with a helper viruses or transfection with plasmids which express all of the appropriate helper functions. This biological characteristic allows rAAV particle recovery by amplification from a target cell. Therefore, subsequent isolation and characterization of viruses expressing desired sequences is accomplished in a rapid and facile manner.

Protocol for generating rAAV-ZFP library

1. Isolate "library" of zinc finger protein inserts from zinc finger protein phage library DNA prep by digesting with Kpn I and Bam HI restriction enzymes.

2. Ligate the Kpn I/Bam HI ZFP-encoding fragment into the above mentioned AAV vectors. Each AAV vector has already been modified to possess the NLS-Kpn I site-Bam HI site-VP16 or KRAB-FLAG. Thereby, the resulting ligations should result in plasmids encoding NLS-ZFPs-KRAB or VP16-FLAG.

3. Starting with the repressor library (KRAB), transform the AAV-ZFP-KRAB plasmids into XL-1 Blue bacteria. Grow overnight on plates.

Figure 4:
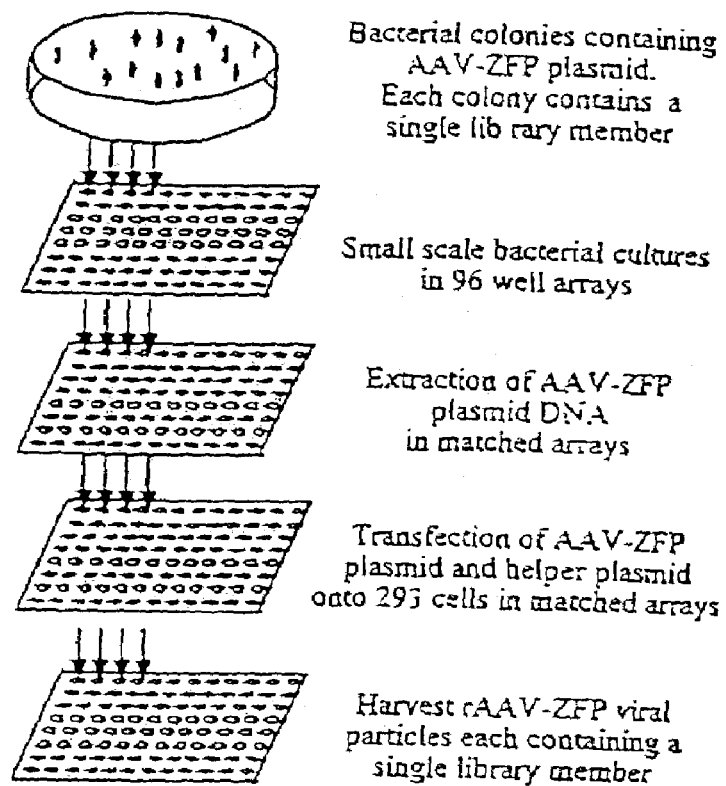
FIG. 4 shows high throughput, arrayed generation of AAV-ZFP vector libraries.
Figure 5:
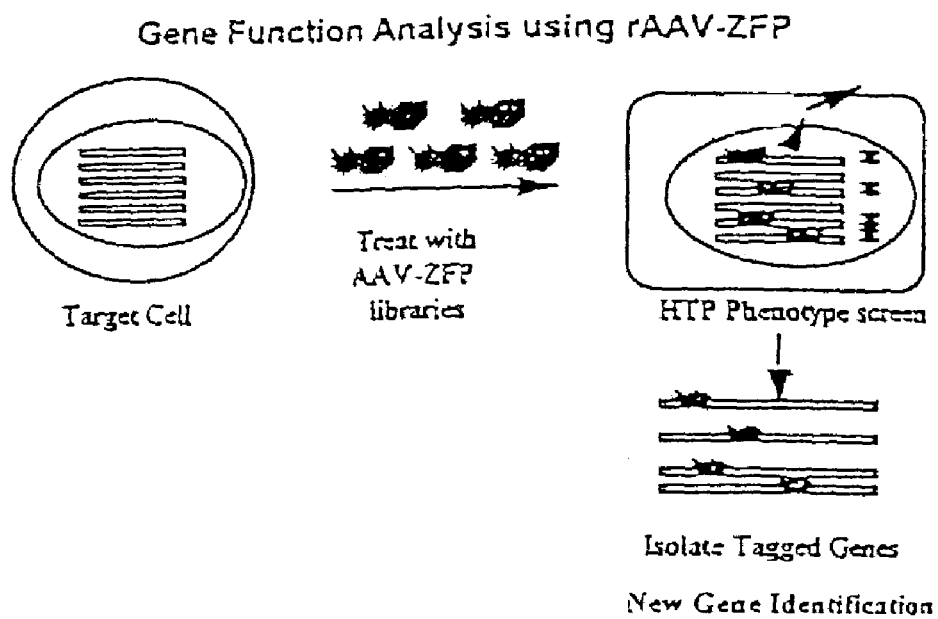
FIG. 5 shows assaying for a phenotype of interest.

4. Pick resulting colonies and array into 96-well format for small-scale bacterial cultures (refer to step 1, FIG. 4).

5. Isolate AAV-ZFP-KRAB plasmids, maintaining the 96-well arrayed format.

6. Plate 293 cells, already stably expressing the AAV rep and cap gene products, in 96-well format. This should be done the day prior to transfection.

7. Infect 293 cells with Adenovirus (Ad), incubate for 1 hour at 37° C.

8. Using the DEAE-Dextran transfection technique, cotransfect the AAV-ZFP-KRAB plasmids along with helper plasmid encoding for the AAV rep and cap gene products. Add the DNA-DEAE-Dextran solution directly to the infected cells. Incubate for 4-5 hours at 37° C. Wash cells and replenish with complete media. Incubate for 72 hours.

9. To recover the resulting AAV-ZFP-KRAB viruses (rAAV-ZFP-KRAB), harvest and lyse the cells (see, e.g., Matsushita et al., *Gene Therapy* 5:938-945 (1998)). Clear the lysate of cellular debris by a low speed centrifugation spin and heat inactivate the Ad virus. The arrays of rAAV-ZFP libraries can be stored at -70° C. until assayed.

C. Selecting a phenotype of interest

The cells transfected with rAAV-ZFPs will each be expressing different genes in different levels, resulting in different phenotypes. Generally, one is interested in a specific phenotype that can be identified easily in a high throughput (HTP) assay. Numerous assays have been developed which can identify changes in cell growth and metabolism. The assay employed depends on the pathway of interest. Once a cell expressing the desired phenotype is identified, the genes expressed/repressed can be determined.

Assay for target discovery using inhibition of VEGF induction during hypoxia

Vascular Endothelial Growth Factor (VEGF) is the principle pro-angiogenic factor responsible for eliciting the growth of new blood supply to hypoxic tissues. VEGF expression is triggered by hypoxia in a wide variety of cell types. This regulation occurs principally at the level of transcription. The hypoxic triggering of VEGF gene expression is central to several important pathologies both in a negative and positive sense. Blockade of VEGF induction could lead to the treatment of solid tumor growth and diabetic retinopathy. Thus, in this example, factors that inhibit hypoxic stimulation of VEGF are identified.

The human embryonic kidney epithelium-derived cell line 293 can be induced to secrete VEGF into the growth medium by making the cells hypoxic or by mimicking hypoxia using cobalt chloride. This induction can be followed using a simple ELISA.

293 cells, previously stably transfected with a gene expressing secreted alkaline phosphatase (SEAP), will be plated in a 96-well format. The cultures will be transduced with the rAAV-ZFP-KRAB library, already arrayed in 96-well format (see above), and allowed to incubate for 48 hours. Next, VEGF expression will be induced using $CoCl_2$. 24 hours post VEGF-induction, culture supernatants will be tested for VEGF secretion. In addition, the secretion of SEAP will be examined as a general control for toxicity and secretion function. Cells that fail to induce VEGF expression will be scored as primary hits.

The zinc finger proteins responsible for the primary hits will be recovered and retested in secondary assays confirming the specific blockade of the VEGF inducing hypoxic signal (Target Validation). In this case, a HTP ELISA is employed to identify the desired phenotypic response in the presence of a specific AAV-ZFP that has targeted a gene involved in hypoxic stimulation of VEGF.

Assay for target discovery using up-regulation of E-cadherin on the cell surface E-cadherin is a focal point in the development of numerous cancers and its function is frequently inactivated in the development of breast, colon, prostate, stomach, liver, esophagus, skin, kidney and lung cancers amongst others. The loss of E-cadherin function is a rate limiting step in the transition of cells from well differentiated adenoma to invasive carcinoma cells. Chromatin rearrangement, mutation, hypermethylation, and loss of transcription-factor binding are all thought to play roles in suppression of E-cadherin function. Furthermore, alterations in function, expression levels, and signaling properties of molecules which associate with E-cadherin have also been shown to play a role in this loss of function. This widespread loss of function in numerous cancer types implies a profound role for E-cadherin in these cancers where it is manifested by de-differentiation, increased infiltrative growth and metastatic potential. Re-establishment of E-cadherin function in various cell culture and in vivo systems has demonstrated the reversion of invasive tumors to a benign, epithelial phenotype. Therefore, in this example, genes which could be invoked to up-regulate E-cadherin expression are identified.

The cell line which will be selected for use in the phenotypic screening assay must be able to express E-cadherin at its surface upon induction of expression by the specifically constructed zinc finger motif. In this case, the HT-29 human colon carcinoma cell line, which has been shown to upregulate E-cadherin expression in response to dimethylsulfoxide (DMSO) in a dose dependent manner, would be appropriate.

Once again, cells are plated in a 96-well format. This time, the cells are transduced with members of a rAA -ZFP-VP16 library, produced as described above. They will be examined for the presence of cell-surface expression of E-cadherin 48 hours post-transduction. Treatment of the cells with DMSO would serve as a positive control.

Determining cell-surface E-cadherin expression can be done by one of several methods. One method is accomplished by binding fluorescently tagged antibodies directed against the E-cadherin on the cell surface. Quantitation of this fluorescence is then detennined by a 96-well fluorometer. Alternatively, a relatively less sensitive immunohistochemical assay performed in a 96 well format may be sufficient for evaluation of up-regulation, supporting the premise of this approach. Another approach to assaying the upregulation of E-cadherin is based on proteolytic digestion of a fluorescence labeled protein substrate. This assay has the potential of being simpler and more sensitive than the one based on using antibodies to detect E-Cadherin expression. It has been shown that in some cancer cell types secreted matrix metalloproteinases are down regulated by the upregulation or reconstitution of E-cadherin expression. In the proposed high throughput assay system, a fluorescently tagged protein substrate (Molecular Probes, EnzChek Assay Kit) does not fluoresce because of the quenching phenomena observed when numerous fluorescent tags are in close proximity to one another. However, when this labeled protein substrate is cleaved by proteases, a fluorescent signal is observed which corresponds to the proteolytic activity in the sample. For screening purposes positive hits would be counted where fluorescence emission is quenched indicating down regulation of protease activity. These positive samples would then be further analyzed and tested for E-cadherin expression.

The up-regulation of E-cadherin would represent the generation of the desired change in tumor cell phenotype induced by the zinc finger protein's action on a gene(s) expression. Thus, indicating that this gene(s) may prove to be a good candidate for drug discovery.

D. Identifying candidate genes associated with a selected phenotype

Once a "hit" has been identified, using, e.g., one of the assays described above, one must then determine the gene(s) the zinc finger protein has influenced that resulted in the desired phenotype. The first step is to identify the zinc finger protein that was involved. This is easily accomplished as indicated in the previous section referring to rAAV recovery. By infecting the cells containing the AAV-ZFP of interest with helper virus, the AAV will enter a lytic cycle and thereby produce progeny virus. Isolation of these rAAV particles from the target cell can be done as previously described. This assures that there is plenty of the rAAV-ZFP for additional experiments and manipulations. Analysis of the zinc finger protein can suggest a putative recognition target site that when compared to sequences listed in GenBank could identify genes that may be affected by the zinc finger protein.

Comparing mRNA of ZFP-transduced vs. non-transduced cells is a direct way of identifying differentially expressed genes. Several methods have been developed to do this sort of analysis: subtractive hybridization, differential display and array analysis, as described above.

What is claimed is:

1. A nucleic acid library encoding randomized zinc finger proteins, wherein the library is generated by recognition helix grafting or by gene shuffling.

2. The library of claim 1, wherein each member of the library further encodes a regulatory domain in operative linkage with the zinc finger protein.

3. The library of claim 2, wherein the regulatory domain is an activation domain.

4. The library of claim 2, wherein the regulatory domain is a repression domain.

5. A eukaryotic cell population transfected with the library of claim 1.

6. The cell population of claim 5, wherein the library is generated by recognition helix grafting.

7. The cell population of claim 5, wherein the library is generated by gene shuffling.

8. The cell population of claim 5, wherein each member of the library further encodes a regulatory domain in operative linkage with the zinc finger protein.

9. The cell population of claim 8, wherein the regulatory domain is an activation domain.

10. The cell population of claim 8, wherein the regulatory domain is a repression domain.

* * * * *